US010444855B2

(12) United States Patent
Isaacs et al.

(10) Patent No.: US 10,444,855 B2
(45) Date of Patent: Oct. 15, 2019

(54) IMAGING SYSTEM AND METHOD FOR USE IN SURGICAL AND INTERVENTIONAL MEDICAL PROCEDURES

(71) Applicant: NuVasive, Inc., San Diego, CA (US)

(72) Inventors: Robert E Isaacs, San Diego, CA (US); Samuel Morris Johnston, San Diego, CA (US); David Alexander Skwerer, San Diego, CA (US); Randall Graham Campbell, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 16/200,519

(22) Filed: Nov. 26, 2018

(65) Prior Publication Data

US 2019/0196599 A1 Jun. 27, 2019

Related U.S. Application Data

(63) Continuation of application No. 15/713,265, filed on Sep. 22, 2017, now Pat. No. 10,139,920, which is a (Continued)

(51) Int. Cl.

*G06F 3/033* (2013.01)
*G06K 9/00* (2006.01)

(Continued)

(52) U.S. Cl.

CPC ................ *G06F 3/017* (2013.01); *A61B 6/06* (2013.01); *A61B 6/12* (2013.01); *A61B 6/4405* (2013.01);

(Continued)

(58) Field of Classification Search

USPC ........ 382/103, 100, 128–134, 153–155, 162, 382/168, 173, 181, 219, 232, 254, 255, (Continued)

(56) References Cited

U.S. PATENT DOCUMENTS 4,367,490 A 1/1983 Riederer
4,641,352 A 2/1987 Fenster et al.

(Continued)

OTHER PUBLICATIONS

Gebhard Schmid et al, "Effective Dose of CT and Fluoroscopy-Guided Perineural/Epidural Injections of the Lumbar Spine: A Comparative Study", Cardiovascular and Interventional Radiology, Springer-Verlag, NE, vol. 29, No. 1, Feb. 1, 2006, pp. 84-91.

(Continued)

*Primary Examiner* — Seyed H Azarian

(57) ABSTRACT

A system and method for displaying images of internal anatomy includes an image processing device configured to provide high resolution images of the surgical field from low resolution scans during the procedure. The image processing device digitally manipulates a previously-obtained high resolution baseline image to produce many representative images based on permutations of movement of the baseline image. During the procedure a representative image is selected having an acceptable degree of correlation to the new low resolution image. The selected representative image and the new image are merged to provide a higher resolution image of the surgical field. The image processing device is also configured to provide interactive movement of the displayed image based on movement of the imaging device, and to permit placement of annotations on the displayed image to facilitate communication between the radiology technician and the surgeon.

17 Claims, 24 Drawing Sheets

Related U.S. Application Data continuation of application No. 14/564,728, filed on Dec. 9, 2014, now Pat. No. 9,785,246, and a continuation-in-part of application No. 14/270,446, filed on May 6, 2014, now Pat. No. 8,908,952, which is a continuation of application No. 13/722,259, filed on Dec. 20, 2012, now Pat. No. 8,718,346, which is a continuation-in-part of application No. 13/253,838, filed on Oct. 5, 2011, now Pat. No. 8,526,700.

(60) Provisional application No. 62/036,660, filed on Aug. 13, 2014, provisional application No. 61/390,488, filed on Oct. 6, 2010.

(51) Int. Cl.

| | |
|---|---|
| ***A61B 5/05*** | (2006.01) |
| ***G06F 3/01*** | (2006.01) |
| ***G06T 3/40*** | (2006.01) |
| ***G06T 11/60*** | (2006.01) |
| ***G06T 7/00*** | (2017.01) |
| ***G06T 15/08*** | (2011.01) |
| ***G06T 7/33*** | (2017.01) |
| ***A61B 6/06*** | (2006.01) |
| ***G06T 3/20*** | (2006.01) |
| ***A61B 6/00*** | (2006.01) |
| ***A61B 6/12*** | (2006.01) |
| ***H04N 7/18*** | (2006.01) |

(52) U.S. Cl.

CPC ............ *A61B 6/4441* (2013.01); *A61B 6/486* (2013.01); *A61B 6/5241* (2013.01); *A61B 6/547* (2013.01); *G06T 3/20* (2013.01); *G06T 3/4053* (2013.01); *G06T 7/0016* (2013.01); *G06T 7/33* (2017.01); *G06T 11/60* (2013.01); *G06T 15/08* (2013.01); *H04N 7/18* (2013.01); *G06T 2207/10124* (2013.01); *G06T 2207/20212* (2013.01); *G06T 2207/20221* (2013.01); *G06T 2207/30004* (2013.01); *G06T 2210/41* (2013.01)

(58) Field of Classification Search

USPC ............... 382/274, 276, 285, 291, 305, 312; 600/426, 424; 378/4, 21, 145, 204; 358/3.26; 715/863

See application file for complete search history.

(56) References Cited

U.S. PATENT DOCUMENTS

| | | | | |
|---|---|---|---|---|
| 5,195,234 | A | 3/1993 | Pine et al. | |
| 5,211,165 | A | 5/1993 | Dumoulin et al. | |
| 5,253,169 | A | 10/1993 | Corby, Jr. | |
| 5,396,531 | A | 3/1995 | Hartley | |
| 5,467,380 | A | 11/1995 | De Jonge et al. | |
| 5,676,673 | A | 10/1997 | Ferre et al. | |
| 5,772,594 | A | 6/1998 | Barrick | |
| 5,901,199 | A | 5/1999 | Murphy et al. | |
| 5,911,012 | A | 6/1999 | Bernard et al. | |
| 5,951,475 | A | 9/1999 | Gueziec et al. | |
| 6,125,164 | A | 9/2000 | Murphy et al. | |
| 6,215,848 | B1 | 4/2001 | Linders et al. | |
| 6,236,875 | B1 | 5/2001 | Bucholz et al. | |
| 6,256,403 | B1 | 7/2001 | Florent et al. | |
| 6,314,160 | B1 | 11/2001 | Dhawale et al. | |
| 6,330,356 | B1 | 12/2001 | Sundareswaran et al. | |
| 6,381,352 | B1 | 4/2002 | Nelson | |
| 6,463,121 | B1 | 10/2002 | Milnes | |
| 6,477,400 | B1 | 11/2002 | Barrick | |
| 6,775,405 | B1 | 8/2004 | Zhu | |
| 6,990,368 | B2 | 1/2006 | Simon et al. | |
| 7,054,474 | B1 | 5/2006 | Krieger | |
| 7,194,117 | B2 | 3/2007 | Kaufman et al. | |
| 7,204,640 | B2 | 4/2007 | Fu et al. | |
| 7,274,771 | B2 | 9/2007 | Allred et al. | |
| 7,317,841 | B2 | 1/2008 | Yatsenko et al. | |
| 7,324,678 | B2 | 1/2008 | Allouche | |
| 7,404,673 | B2 | 7/2008 | Hornig | |
| 7,505,617 | B2 | 3/2009 | Fu et al. | |
| 7,526,065 | B2 * | 4/2009 | Hardesty | A61B 6/542 378/145 |
| 7,599,575 | B2 * | 10/2009 | Lienard | G06T 5/002 358/3.26 |
| 7,603,155 | B2 | 10/2009 | Jensen | |
| 7,658,541 | B2 * | 2/2010 | Li | A61B 6/06 378/204 |
| 7,672,709 | B2 | 3/2010 | Lavallee et al. | |
| 7,817,834 | B2 | 10/2010 | Bernhardt et al. | |
| 7,848,592 | B2 | 12/2010 | Chen et al. | |
| 7,853,305 | B2 * | 12/2010 | Simon | A61B 6/12 600/424 |
| 7,856,130 | B2 | 12/2010 | Suri et al. | |
| 7,885,441 | B2 * | 2/2011 | Node-Langlois | G06T 7/74 382/128 |
| 2005/0047544 | A1 | 3/2005 | Fu et al. | |
| 2005/0272991 | A1 | 12/2005 | Xu et al. | |
| 2006/0002630 | A1 | 1/2006 | Fu et al. | |
| 2006/0116575 | A1 | 6/2006 | Willis | |
| 2006/0293592 | A1 | 12/2006 | Jensen | |
| 2007/0189603 | A1 | 8/2007 | Kasperkiewicz et al. | |
| 2008/0269602 | A1 * | 10/2008 | Csavoy | A61B 90/18 600/426 |
| 2009/0324041 | A1 | 12/2009 | Narayanan et al. | |
| 2009/0326363 | A1 | 12/2009 | Li et al. | |
| 2010/0001996 | A1 | 1/2010 | Shen et al. | |
| 2010/0004526 | A1 | 1/2010 | Wei et al. | |
| 2010/0004530 | A1 | 1/2010 | Kumar et al. | |
| 2010/0207942 | A1 | 8/2010 | Zhao | |
| 2011/0152676 | A1 | 6/2011 | Groszmann et al. | |

OTHER PUBLICATIONS

Ma Jianhua et al: "Low-dose computed tomography image restoration using previous normal-dose scan", Medical Physics, AIP, Melville, NY, US, vol. 38, No. 10, Oct. 1, 2011, pp. 5713-5731.

Navas Net al: "Merging visible and invisible: two Camera-Augmented Mobile C-arm (CAMC) applications", Augmented Reality, 1999. (IWAR '99). Proceedings. 2nd IEEE and ACM International Workshop on San Francisco, CA, USA Oct. 20-21, 1999, Los Alamitos, CA, USA, IEEE Comput. Soc, US, Oct. 20, 1999, pp. 134-141.

Metz, C.T. et al. "GPU Accelerated Alignment of 3-D CTA with 2-D X-Ray Data for Improved Guidance in Coronary Interventions," IEEE 2009, pp. 959-962.

Gong, Ren Hui and Abolmaesumi, Pu Rang, "2D/3D Registration with the CMA-ES Method," Proceedings of SPIE, vol. 6918, 69181M, 2008.

Cheryauka, Arvi, Barred, Johnny and Wang, Zhonghua, "3-D Geometry Calibration and Markerless Electromagnetic Tracking with a Mobile C-arm," Proceedings of SPIE, vol. 6509, 650927-1, 2007.

West, Jay B. and Maurer, Calvin R., Jr., "A System for Finding a 3D Target Without a 3D Image," Proceedings of SPIE, vol. 691869180J-1, 2008.

Wilson, Emmanuel, Yaniv, Ziv, Lindisch, David and Cleary, Kevin, "A Buyer's Guide to Electromagneti Tracking System for Clinical Applications," Proceedings of SPIE, vol. 6918, 69182B-1, 2008.

Koishi, Takeshi, et al., "A Navigation System Using Projection Images of Laparoscopic Instruments and a Surgi Target with Improved Image Quality," Proceedings of SPIE, vol. 6918, 691810-1, 2008.

Kwartowitz, David M., et al, "A Novel Technique for Analysis of Accuracy of Magnetic Tracking Systems Used in Image Guided Surgery," Proceedings of SPIE, vol. 7625 76251 L-1, 2010.

Ding, Jienan, et al., "Accuracy Analysis of an Image-Guided System for Vertebroplasty Spinal Therapy Based on Electromagnetic Tracking of Instruments," Proceedings of SPIE, vol. 6918 69181 K-1, 2008.

(56) References Cited

OTHER PUBLICATIONS

Brost, Alexander, et al., "Accuracy of X-Ray Image-Based 3D Localization from Two C-Arm Views: A Comparison Between an Ideal System and a Real Device," Proceedings of SPIE, vol. 7261 72611Z-1, 2009.
Jomier, Julien, et al., "An Open-Source Framework for Testing Tracking Devices Using Lego Mindslorms," Proceedings of SPIE, vol. 7261 72612S-1, 2009.
Foroughi, Pezhman, Taylor, Russell H. and Fichtinger, Gabor, "Automatic Initialization of3D Bone Registration," Proceedings ofSPIE, vol. 6918, 69182P-1, 2008.
Jain, Ameet Kumar, et al., "C-arm Calibration—is ii Really Necessary?" Proceedings of SPIE, vol. 6509 65092U-1, 2007.
Mori, Kensaku, et al., "Compensation of Electromagnetic Tracking System Using an Optical Tracker and its Application to Bronchoscopy Navigation System," Proceedings of SPIE, vol. 6509 65090M-1, 2007.
Hagedorn, John G., et al., "Correction of Location and Orientation Errors in Electromagnetic Motion Tracking," Presence, vol. 16, No. 4, Aug. 2007, pp. 352-366.
Lu, J., Egger, J., Wimmer, A., Grobkoph, S. and Freisleben, B., "Detection and Visualization of Endoleaks ir CT Data for Monitoring of Thoracic and Abdominal Aortic Aneurysm Stents," Proceedings of SPIE, vol. 6918 69181F-1, 2008.
Schneider, Mark and Stevens, Charles, "Development and Testing of a New Magnetic-Tracking Device for Image Guidelines," Proceedings of SPIE, vol. 6509 650901-1, 2007.
Robler, Friedmann, et al., "Distributed Video Generation on a GPU-Ciuster for the Web-Based Analysis of Medical Image Data," Proceedings of SPIE, vol. 6509 650903-1, 2007.
Shen, Eric, et al., "Effects of Sensor Orientation on AC Electromagnetic Tracking System Accuracy in aCT Scanner Environment," Proceedings of SPIE, vol. 6918 691823-1, 2008.
Nagel, Markus, et al., "Electromagnetic Tracking System for Minimal Invasive Interventions Using AC-Arm System With CT Options: First Clinical Results," Proceedings of SPIE, vol. 6918 69180G-1, 2008.
Hummel, Johann, et al., "Evaluation of Dynamic Electromagnetic Tracking Deviation," Proceedings of SPIE, vol. 726172612U-1 ,2009.
Seslija, Pet Ar, et al., "Feasibility of 3D Tracking of Surgical Tools Using 2D Single Plane X-Ray Projections," Proceedings of SPIE, vol. 691B 69180K-1, 2008.
Fitzpatrick, J. Michael, "Fiducial Registration Error and Target Registration Error Are Uncorrelated," Proceedings of SPIE, Vo. 7261726102-1,2009.
Chung, Adrian, J., et al., "Freehand Cocalibration of Optical and Electromagnetic Trackers for Navigated Bronchoscopy," LNCS 3150, pp. 320-328, 2004.
Siewerdsen, J.H., et al., "High-Performance Intraoperative Cone-Beam CT on a Mobile C-Arm: An Integrated System for Guidance of Head and Neck Surgery," Proceedings of SPIE, vol. 7261 7261OJ-1, 2009.
McDonald, Colin P., et al.,"Implant Alignment in Total Elbow Arthroplasty: Conventional vs. Navigated Techniques," Proceedings of SPIE, vol. 7261 726112-1, 2009.
Liao, Rui, Xu, Ning, Sun, Yiyong, "Location Constraint Based 2D-3D Registration of Fluoroscopic Images and Volumes for Image-Guided EP Procedures," Proceedings of SPIE, vol. 6918 69182T-1, 2008.
Moghari, Mehdi Hedjazi and Abolmaesumi, Purang,"Maximum Likelihood Estimation of the Distribution Target Registration Error," Proceedings of SPIE, vol. 6918 691801-1, 2008.
Albers, Rob, Suijs, Eric and de With, Peter H. N., "Memory-Efficient 3D Multi-Resolution Image Enhancement and Processing to Increase Throughput," Proceedings of SPIE, vol. 6918 69182Y-1, 2008.
Nafis, Christopher, Jensen, Vern and Von Jako, Ron, "Method for Evaluating Compatibility of Commercial Electromagnetic (EM) Micro Sensor Tracking Systems With Surgical and Imaging Tables," General Electric.
Nagel, Markus, et al., "Needle and Catheter Navigation Using Electromagnetic Tracking for Computer-Assisted C-Arm CT Intervention," Proceedings of SPIE, vol. 6509 65090J-1, 2007.
Kindratenko, Volodymry and Sherman, William R., "Neural Network-Based Calibration of Electromagnetic Tracking System," Virtual Reality, 2006, 9, pp. 70-78.
Lin, Ralph, et al., "Phantom Evaluation of an Image-Guided Navigation System Based on Electromagnetic Tracking and Open Source Software," Proceedings of SPIE, vol. 6918 691826-1, 2008.
Shen, Eric, et al., "Quantification of AC Electromagnetic Tracking System Accuracy in aCT Scanner Environment," Proceedings of SPIE, vol. 6509 65090L-1, 2007.
Worz, S., et al., "Quantification of the Aortic Arch Morphology in 3D CTA Images for Endovascular Aortic Repair (EVAR)," Proceedings of SPIE, vol. 6918 69181 H-1, 2008.
Zagorchev, L Yu Bo Mir, et al., "Rapid Fusion of 2D X-Ray Fluoroscopy with 3D Multislice CT for Image-Guided Electrophysiology Procedures," Proceedings of SPIE, vol. 6509 650928-1, 2007.
Kirsch, Stefan R., et al., "Assessment of Metallic Distortions of an Electromagnetic Tracking System," Proceedings ofSPIE, vol. 6141, 61410J, 2006.
Yaniv, Ziv and Cleary, Kevin, "Fluoroscopy Based Accuracy Assessment of Electromagnetic Tracking," Proceedings of SPIE, vol. 6141, 61410L, 2006.
Kindratenko, Volodymyr V., "A Survey of Electromagnetic Position Tracker Calibration Techniques," Virtual Reality: Research, Development and Applications, 2000, vol. 5, No. 3, pp. 169-182.
Schaller, Christian, et al., "Time-of-Flight Sensor for Patient Positioning," Proceedings of SPIE, vol. 7261 726110-1, 2009.
Spiegel, Martin, et al., "Towards Real-Tim Guidewire Detection and Tracking in the Field of Neuroradiology," Proceedings ofSPIE, vol. 7261726105-1,2009.
Ikits, Milan, et al., "An Improved Calibration Framework for Electromagnetic Tracking Devices," Scientific Computing and Imaging Institute, School of Computing University of Utah.
Murphy et al., "The Management of Imaging Dose During Image-Guided Radiotherapy," Medical Physics, vol. 34, No. 10, Oct. 2007 (pp. 4041-4063).
Metz, C.T.,"Digitally Reconstructed Radiographs," Sep. 13, 2005, http://bigr.nl/files/publications/321_DRR.pdf. (83 pages).
International Search Report corresponding to PCT/US12/58845, dated Feb. 26, 2013 (13 pages).

* cited by examiner

Pulsed Low Dose
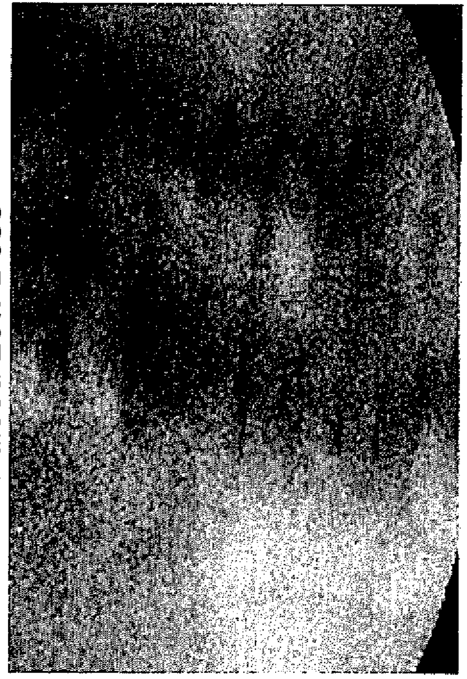
Fig. 2B
Full Dose
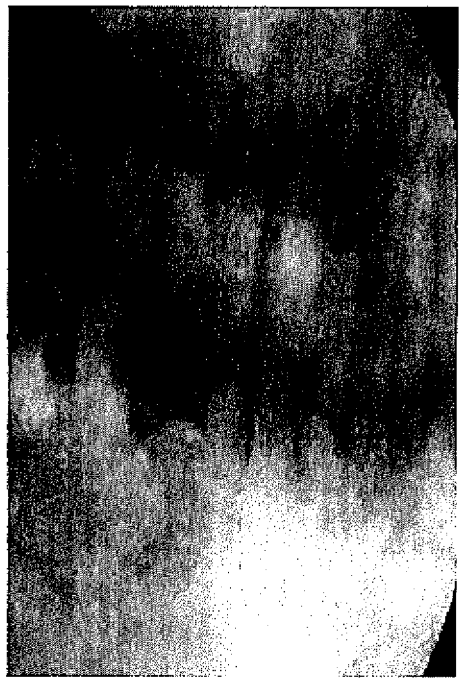
Fig. 2A
Fig. 2C

The Raw Image

GE OEC WORKSHOP
03/24/2012
10:43:11 AM

9 INCH PULSE 1

69 kVp
0.64 mA
49

OEC

Fig. 4A

Edge Enhancement with Butterworth Filters

Image Statistics

5x5 local standard deviation

3x3 local standard deviation

5x5 gradient

3x3 gradient

Image Statistics local standard deviation
of gradient local standard deviation
of local standard deviation gradient
of gradient gradient
of local standard deviation Lookup Table Mask Threshold Mask Lookup Table Mask after Dilation and Erosion Threshold Mask after Dilation and Erosion Threshold Mask Applied to Filtered Image Lookup Table Mask Applied to Filtered Image

IMAGING SYSTEM AND METHOD FOR USE IN SURGICAL AND INTERVENTIONAL MEDICAL PROCEDURES

CROSS-REFERENCE TO RELATED APPLICATION

This application claims priority to and is a continuation of U.S. application Ser. No. 15/713,265, filed Sep. 22, 2017 (currently pending), which claims priority to and is a continuation of U.S. application Ser. No. 14/564,728, filed Dec. 9, 2014, and issued on Oct. 10, 2017 as U.S. Pat. No. 9,785,246, which claims priority to and is a continuation-in-part of U.S. application Ser. No. 14/270,446, filed on May 6, 2014, and issued on Dec. 9, 2014 as U.S. Pat. No. 8,908,952, which is a continuation of U.S. application Ser. No. 13/722,259, filed on Dec. 20, 2012, and issued on May 6, 2014, as U.S. Pat. No. 8,718,346, which is a continuation-in-part of U.S. application Ser. No. 13/253,838, filed on Oct. 5, 2011, and issued on Sep. 3, 2013, as U.S. Pat. No. 8,526,700, which was a non-provisional of Provisional Application No. 61/390,488, filed on Oct. 6, 2010, the entire disclosures of which are incorporated herein by reference. U.S. application Ser. No. 14/564,728 is also a non-provisional of and further claims priority to Provisional Application No. 62/036,660, filed on Aug. 13, 2014, the entire disclosure of which is incorporated herein by reference.

BACKGROUND

The present invention contemplates a system and method for altering the way a patient image, such as by X-ray, is viewed and obtained. More particularly, the inventive system and method provides means for decreasing the overall radiation to which a patient is exposed during a surgical procedure but without significantly sacrificing the quality or resolution of the image obtained.

Many surgical procedures require obtaining an image of the patient's internal body structure, such as organs and bones. In some procedures, the surgery is accomplished with the assistance of periodic images of the surgical site. Surgery can broadly mean any invasive testing or intervention performed by medical personnel, such as surgeons, interventional radiologists, cardiologists, pain management physicians, and the like. In surgeries and interventions that are in effect guided by serial imaging, which we will refer to as image guided, frequent patient images are necessary for the physician's proper placement of surgical instruments, be they catheters, needles, instruments or implants, or performance of certain medical procedures. Fluoroscopy, or fluoro, is one form of intraoperative X-ray and is taken by a fluoro unit, also known as a C-arm. The C-arm sends X-ray beams through a patient and takes a picture of the anatomy in that area, such as skeletal and vascular structure. It is, like any picture, a two-dimensional (2D) image of a three-dimensional (3D) space. However, like any picture taken with a camera, key 3D info may be present in the 2D image based on what is in front of what and how big one thing is relative to another.

A DRR is a digital representation of an X-ray made by taking a CT scan of a patient and simulating taking X-rays from different angles and distances. The result is that any possible X-ray that can be taken for that patient can be simulated, which is unique and specific to how the patient's anatomical features look relative to one another. Because the "scene" is controlled, namely by controlling the virtual location of a C-Arm to the patient and the angle relative to one another, a picture can be generated that should look like any X-ray taken in the operating room (OR).

Many imaging approaches, such as taking fluoro images, involve exposing the patient to radiation, albeit in small doses. However, in these image guided procedures, the number of small doses adds up so that the total radiation exposure can be problematic not only to the patient but also to the surgeon or radiologist and others participating in the surgical procedure. There are various known ways to decrease the amount of radiation exposure for a patient/surgeon when an image is taken, but these approaches come at the cost of decreasing the resolution of the image being obtained. For example, certain approaches use pulsed imaging as opposed to standard imaging, while other approaches involve manually altering the exposure time or intensity. Narrowing the field of view can potentially also decrease the area of radiation exposure and its quantity (as well as alter the amount of radiation "scatter") but again at the cost of lessening the information available to the surgeon when making a medical decision. Collimators are available that can specially reduce the area of exposure to a selectable region. For instance, a collimator, such as the Model Series CM-1000 of Heustis Medical, is placed in front of an x-ray source, such as the source 104 shown in FIG. 1. The collimator consists of a series of plates that absorb most incident X-rays, such as lead. The only x-rays that reach the patient are those that pass through apertures between the plates. The position of the plates can be controlled manually or automatically, and the plates may be configured to provide differently shaped fields, such a multi-sided field. Since the collimator specifically excludes certain areas of the patient from exposure to x-rays, no image is available in those areas. The medical personnel thus have an incomplete view of the patient, limited to the specifically selected area. Thus, while the use of a collimator reduces the radiation exposure to the patient, it comes at a cost of reducing the amount of information available to the medical personnel.

Further, often times images taken during a surgical intervention are blocked either by extraneous OR equipment or the actual instruments/implants used to perform the intervention. Limiting the blocking of the normal anatomy behind those objects would have tangible benefits to the medical community.

There is a need for a an imaging system, that can be used in connection with standard medical procedures, that reduces the radiation exposure to the patient and medical personnel, but without any sacrifice in accuracy and resolution of an X-ray image. There is also a need for an imaging system that accounts for instruments and hardware, such as implants, that might otherwise obscure a full view of the surgical site.

SUMMARY

According to one aspect, a system and method is providing for generating a display of a patient's internal anatomy for use in a surgical or interventional medical procedure based on a previously acquired high resolution baseline image and a newly acquired low resolution image. The high resolution image may be an image obtained during the procedure or a pre-procedure image such as a DRR. The low resolution image may be acquired using a pulse and/or low dose radiation setting. The system contemplates an image processing device configured to digitally manipulate the high resolution baseline image to produce a baseline image set including representative images of the baseline image at a plurality of permutations of movements of the baseline image in 4D or 6D space. The new low resolution image is compared to the baseline image set to select a representative image having an acceptable degree of correlation with the new image. The image processing device may implement algorithms to perform the comparison, such as a principal component analysis or other statistical test. The image processing device is further configured to merge the selected representative high resolution image with the new low resolution image to generate a merged image to be displayed. The merged image may be further processed to allow alternating between the selected high resolution image and the new low resolution image, or to adjust the amount that the two images are merged in the displayed image.

In another feature of the present disclosure, an imaging system may include an image processing device that acts as a viewfinder as the imaging device is moved relative to the patient. In accordance with this feature, an image of the surgical field is acquired with the imaging device in a first orientation. That acquired image is continuously displayed while the imaging device, patient or patient table is moved from the first orientation. This movement is tracked is used the image processing device to move the displayed image in relation to the tracked movement. With this feature, the display acts as a viewfinder to predict how a new image would appear if captured at that time by the imaging device. This feature can thus be used to determine where the next live image of the patient's anatomy will be taken or can be used to assist in stitching multiple images together to form a larger panoramic view of the surgical field. The image processing system may implement software adapted to optimize the predicted image and minimize misalignment or off angle appearance of the display. In another aspect, the image processing system permits annotation of the displayed image to identify anatomic features or desired image trajectories or alignments.

In a further feature of the disclosed embodiments, a baseline image of anatomy within a surgical field is acquired in a baseline orientation, and that baseline image is digitally manipulated to produce a baseline image set including representative images of the baseline image at a plurality of permutations of movements of the baseline image. A new image of the surgical field in which portions of the anatomy are blocked by objects. This new image is compared to the baseline image set to select a representative image having an acceptable degree of correlation with the new image. The image processing system generates a displayed image showing the surgical field with the blocking objects minimized or eliminated. The system further permits fading the blocked objects in and out of the display.

BRIEF DESCRIPTION OF THE DRAWINGS

FIG. 2A is an image of a surgical field acquired using a full dose of radiation in the imaging system.

FIG. 2B is an image of the surgical field shown in FIG. 2A in which the image was acquired using a lower dose of radiation.

FIG. 2C is a merged image of the surgical field with the two images shown in FIGS. 2A-B merged in accordance with one aspect of the present disclosure.

FIG. 4A is an image of a surgical field including an object blocking a portion of the anatomy.

DETAILED DESCRIPTION

Figure 1:
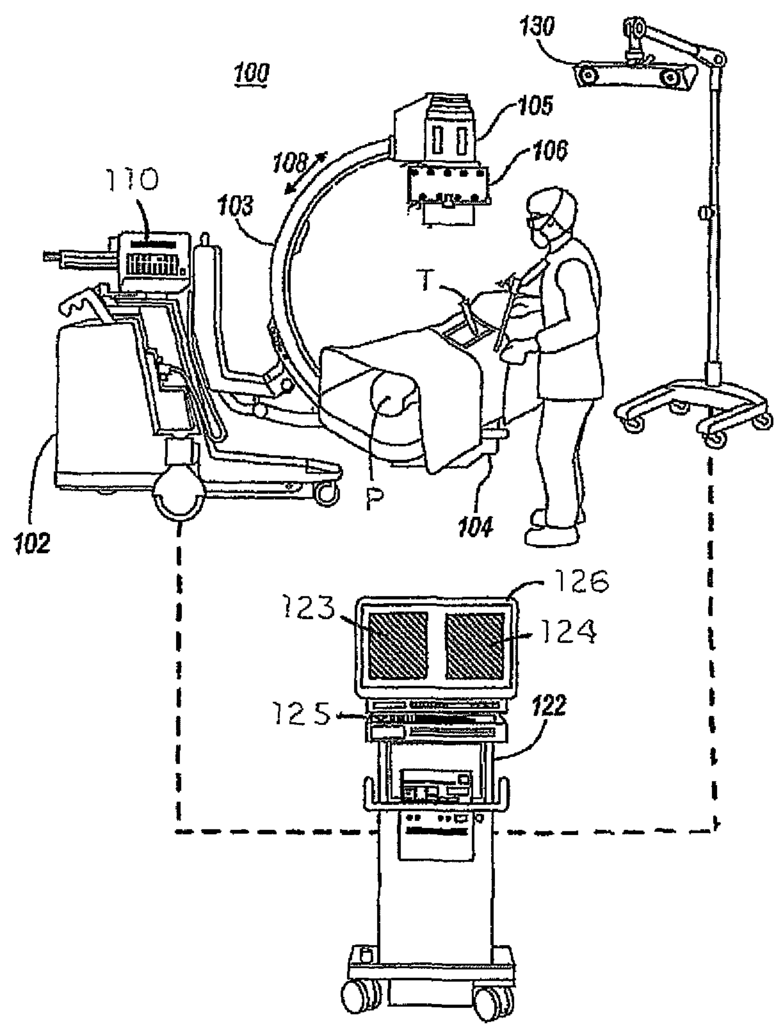
FIG. 1 is a pictorial view of an image guided surgical setting including an imaging system and an image processing device, as well as a tracking device.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

A typical imaging system 100 is shown in FIG. 1. The imaging system includes a base unit 102 supporting a C-arm imaging device 103. The C-arm includes a radiation source 104 that is positioned beneath the patient P and that directs a radiation beam upward to the receiver 105. It is known that the radiation beam emanated from the source 104 is conical so that the field of exposure may be varied by moving the source closer to or away from the patient. The source 104 may include a collimator that is configured to restrict the field of exposure. The C-arm 103 may be rotated about the patient P in the direction of the arrow 108 for different viewing angles of the surgical site. In some instances, implants or instruments T may be situated at the surgical site, necessitating a change in viewing angle for an unobstructed view of the site. Thus, the position of the receiver relative to the patient, and more particularly relative to the surgical site of interest, may change during a procedure as needed by the surgeon or radiologist. Consequently, the receiver 105 may include a tracking target 106 mounted thereto that allows tracking of the position of the C-arm using a tracking device 130. For instance, the tracking target 106 may include several infrared emitters spaced around the target, while the tracking device is configured to triangulate the position of the receiver 105 from the infrared signals emitted by the element. The base unit 102 includes a control panel 110 through which a radiology technician can control the location of the C-arm, as well as the radiation exposure. A typical control panel 110 thus permits the technician to "shoot a picture" of the surgical site at the surgeon's direction, control the radiation dose, and initiate a radiation pulse image.

The receiver 105 of the C-arm 103 transmits image data to an image processing device 122. The image processing device can include a digital memory associated therewith and a processor for executing digital and software instructions. The image processing device may also incorporate a frame grabber that uses frame grabber technology to create a digital image for projection as displays 123, 124 on a display device 126. The displays are positioned for interactive viewing by the surgeon during the procedure. The two displays may be used to show a images from two views, such as lateral and AP, or may show a baseline scan and a current scan of the surgical site, or a current scan and a "merged" scan based on a prior baseline scan and a low radiation current scan, as described herein. An input device 125, such as a keyboard or a touch screen, can allow the surgeon to select and manipulate the on-screen images. It is understood that the input device may incorporate an array of keys or touch screen icons corresponding to the various tasks and features implemented by the image processing device 122. The image processing device includes a processor that converts the image data obtained from the receiver 105 into a digital format. In some cases the C-arm may be operating in the cinematic exposure mode and generating many images each second. In these cases, multiple images can be averaged together over a short time period into a single image to reduce motion artifacts and noise.

In one aspect of the present invention, the image processing device 122 is configured to provide high quality real-time images on the displays 123, 124 that are derived from lower detail images obtained using lower doses (LD) of radiation. By way of example, FIG. 2A is a "full dose" (FD) x-ray image, while FIG. 2B is a low dose and/or pulsed (LD) image of the same anatomy. It is apparent that the LD image is too "noisy" and does not provide enough information about the local anatomy for accurate image guided surgery. While the FD image provides a crisp view of the surgical site, the higher radiation dose makes taking multiple FD images during a procedure highly problematic. Using the steps described herein, the surgeon is provided with a current image shown in FIG. 2C that significantly reduces the noise of the LD image, in some cases by about 90%, so that surgeon is provided with a clear real-time image using a pulsed or low dose radiation setting. This capability allows for dramatically less radiation exposure during the imaging to verify the position of instruments and implants during the procedure.

Figure 3:
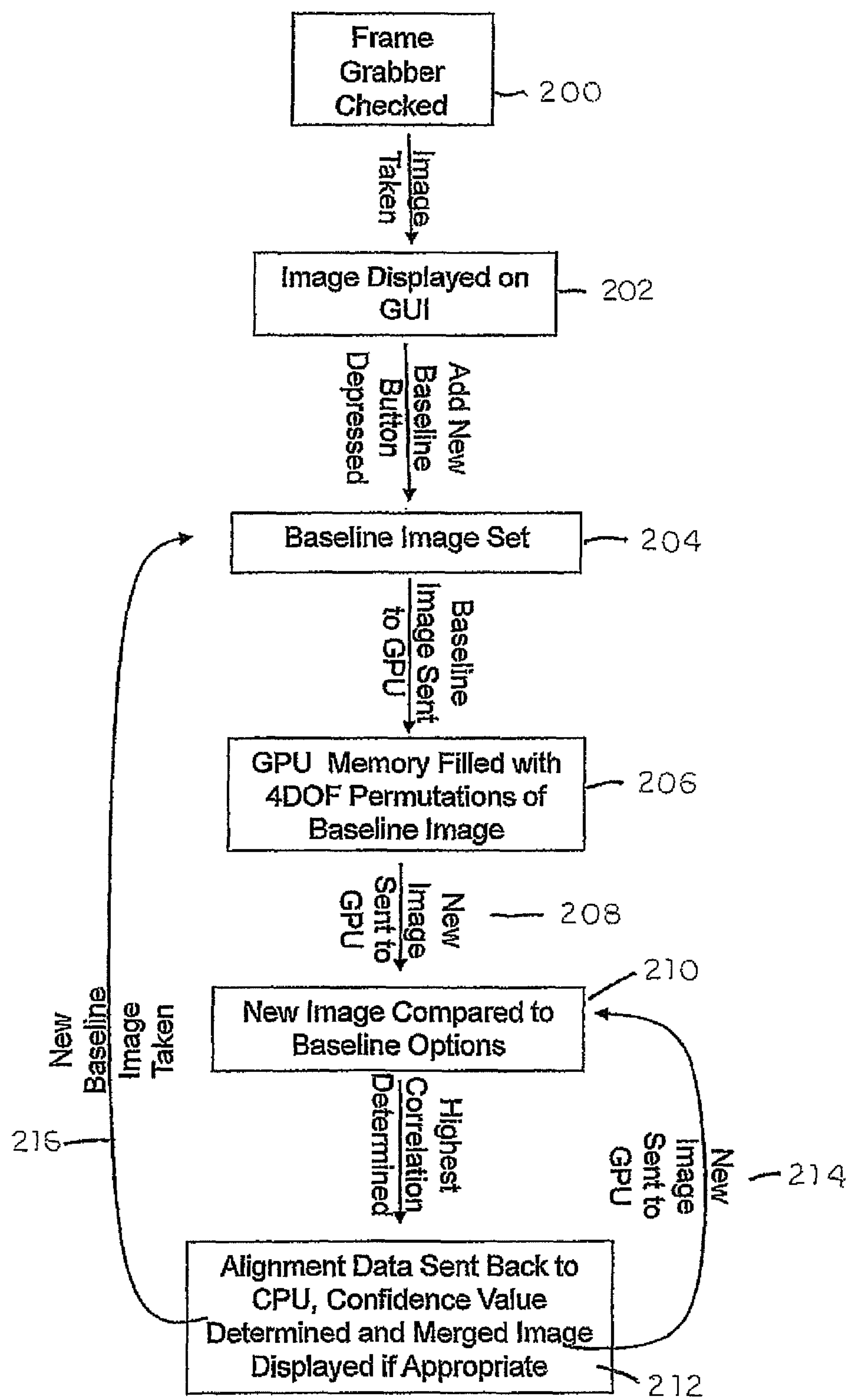
FIG. 3 is a flowchart of graphics processing steps undertaken by the image processing device shown in FIG. 1.

The flowchart of FIG. 3 depicts one embodiment of method according to the present invention. In a first step 200, a baseline high resolution FD image is acquired of the surgical site and stored in a memory associated with the image processing device. In some cases where the C-arm is moved during the procedure, multiple high resolution images can be obtained at different locations in the surgical site, and then these multiple images "stitched" together to form a composite base image using known image stitching techniques). Movement of the C-arm, and more particularly "tracking" the acquired image during these movements, is accounted for in other steps described in more detail herein. For the present discussion it is assumed that the imaging system is relative fixed, meaning that only very limited movement of the C-arm and/or patient are contemplated, such as might arise in an epidural pain procedure, spinal K-wire placement or stone extraction. The baseline image is projected in step 202 on the display 123 for verification that the surgical site is properly centered within the image. In some cases, new FD images may be obtained until a suitable baseline image is obtained. In procedures in which the C-arm is moved, new baseline images are obtained at the new location of the imaging device, as discussed below. If the displayed image is acceptable as a baseline image, a button may be depressed on a user interface, such as on the display device 126 or interface 125. In procedures performed on anatomical regions where a substantial amount of motion due to physiological processes (such as respiration) is expected, multiple baseline images may be acquired for the same region over multiple phases of the cycle. These images may be tagged to temporal data from other medical instruments, such as an ECG or pulse oximeter.

Once the baseline image is acquired, a baseline image set is generated in step 204 in which the original baseline image is digitally rotated, translated and resized to create thousands of permutations of the original baseline image. For instance, a typical two dimensional (2D) image of 128×128 pixels may be translated±15 pixels in the x and y directions at 1 pixel intervals, rotated ±9° at 3° intervals and scaled from 92.5% to 107.5% at 2.5% intervals (4 degrees of freedom, 4D), yielding 47,089 images in the baseline image set. (A three-dimensional (3D) image will imply a 6D solution space due to the addition of two additional rotations orthogonal to the x and y axis. An original CT image data set can be used to form many thousands of DRRs in a similar fashion.) Thus, in this step, the original baseline image spawns thousands of new image representations as if the original baseline image was acquired at each of the different movement permutations. This "solution space" may be stored in a graphics card memory, such as in the graphics processing unit (GPU) of the image processing device 122, in step 206 or formed as a new image which is then sent to the GPU, depending on the number of images in the solution space and the speed at which the GPU can produce those images. With current computing power, on a free standing, medical grade computer, the generation of a baseline image set having nearly 850,000 images can occur in less than one second in a GPU because the multiple processors of the GPU can each simultaneously process an image.

During the procedure, a new LD image is acquired in step 208, stored in the memory associated with the image processing device, and projected on display 123. Since the new image is obtained at a lower dose of radiation it is very noisy. The present invention thus provides steps for "merging" the new image with an image from the baseline image set to produce a clearer image on the second display 124 that conveys more useful information to the surgeon. The invention thus contemplates an image recognition or registration step 210 in which the new image is compared to the images in the baseline image set to find a statistically meaningful match. A new "merged" image is generated in step 212 that may be displayed on display 124 adjacent the view of the original new image. At various times throughout the procedure, a new baseline image may be obtained in step 216 that is used to generate a new baseline image set in step 204.

Step 210 contemplates comparing the current new image to the images in the baseline image set. Since this step occurs during the surgical procedure, time and accuracy are critical. Preferably, the step can obtain an image registration in less than one second so that there is no meaningful delay between when the image is taken by the C-arm and when the merged image is displayed on the device 126. Various algorithms may be employed that may be dependent on various factors, such as the number of images in the baseline image set, the size and speed of the computer processor or graphics processor performing the algorithm calculations, the time allotted to perform the computations, and the size of the images being compared (e.g., 128×128 pixels, 1024×1024 pixels, etc). In one approach, comparisons are made between pixels at predetermined locations described above in a grid pattern throughout 4D space. In another heuristic approach, pixel comparisons can be concentrated in regions of the images believed to provide a greater likelihood of a relevant match. These regions may be "pre-seeded" based on knowledge from a grid or PCA search (defined below), data from a tracking system (such as an optical surgical navigation device), or location data from the DICOM file or the equivalent. Alternatively, the user can specify one or more regions of the image for comparison by marking on the baseline image the anatomical features considered to be relevant to the procedure. With this input each pixel in the region can be assigned a relevance score between 0 and 1 which scales the pixel's contribution to the image similarity function when a new image is compared to the baseline image. The relevance score may be calibrated to identify region(s) to be concentrated on or region(s) to be ignored.

In another approach, a principal component analysis (PCA) is performed, which can allow for comparison to a larger number of larger images in the allotted amount of time than is permitted with the full resolution grid approach. In the PCA approach, a determination is made as to how each pixel of the image set co-varies with each other. A covariance matrix may be generated using only a small portion of the total solution set—for instance, a randomly selected 10% of the baseline image set. Each image from the baseline image set is converted to a column vector. In one example, a 70×40 pixel image becomes a 2800×1 vector. These column vectors are normalized to a mean of 0 and a variance of 1 and combined into a larger matrix. The covariance matrix is determined from this larger matrix and the largest eigenvectors are selected. For this particular example, it has been found that 30 PCA vectors can explain about 80% of the variance of the respective images. Thus, each 2800×1 image vector can be multiplied by a 2800×30 PCA vector to yield a 1×30 vector. The same steps are applied to the new image—the new image is converted to a 2800×1 image vector and multiplication with the 2800×30 PCA vector produces a 1×30 vector corresponding to the new image. The solution set (baseline image) vectors and the new image vector are normalized and the dot product of the new image vector to each vector in the solution space is calculated. The solution space baseline image vector that yields the largest dot product (i.e., closest to 1) is determined to be the closest image to the new image. It is understood that the present example may be altered with different image sizes and/or different principal components used for the analysis. It is further understood that other known techniques may be implemented that may utilize eigenvectors, singular value determination, mean squared error, mean absolute error, and edge detection, for instance. It is further contemplated that various image recognition approaches can be applied to selected regions of the images or that various statistical measures may be applied to find matches falling within a suitable confidence threshold. A confidence or correlation value may be assigned that quantifies the degree of correlation between the new image and the selected baseline image, or selected ones of the baseline image set, and this confidence value may be displayed for the surgeon's review. The surgeon can decide whether the confidence value is acceptable for the particular display and whether another image should be acquired.

In the image guided surgical procedures, tools, implants and instruments will inevitably appear in the image field. These objects are typically radiodense and consequently block the relevant patient anatomy from view. The new image obtained in step 210 will thus include an artifact of the tool T that will not correlate to any of the baseline image set. The presence of the tool in the image thus ensures that the comparison techniques described above will not produce a high degree of registration between the new image and any of the baseline image set. Nevertheless, if the end result of each of the above procedures is to seek out the highest degree of correlation, which is statistically relevant or which exceeds a certain threshold, the image registration may be conducted with the entire new image, tool artifact and all.

Alternatively, the image registration steps may be modified to account for the tool artifacts on the new image. In one approach, the new image may be evaluated to determine the number of image pixels that are "blocked" by the tool. This evaluation can involve comparing a grayscale value for each pixel to a threshold and excluding pixels that fall outside that threshold. For instance, if the pixel grayscale values vary from 0 (completely blocked) to 10 (completely transparent), a threshold of 3 may be applied to eliminate certain pixels from evaluation. Additionally, when location data is available for various tracked tools, algorithmically areas that are blocked can be mathematically avoided.

Figure 11:
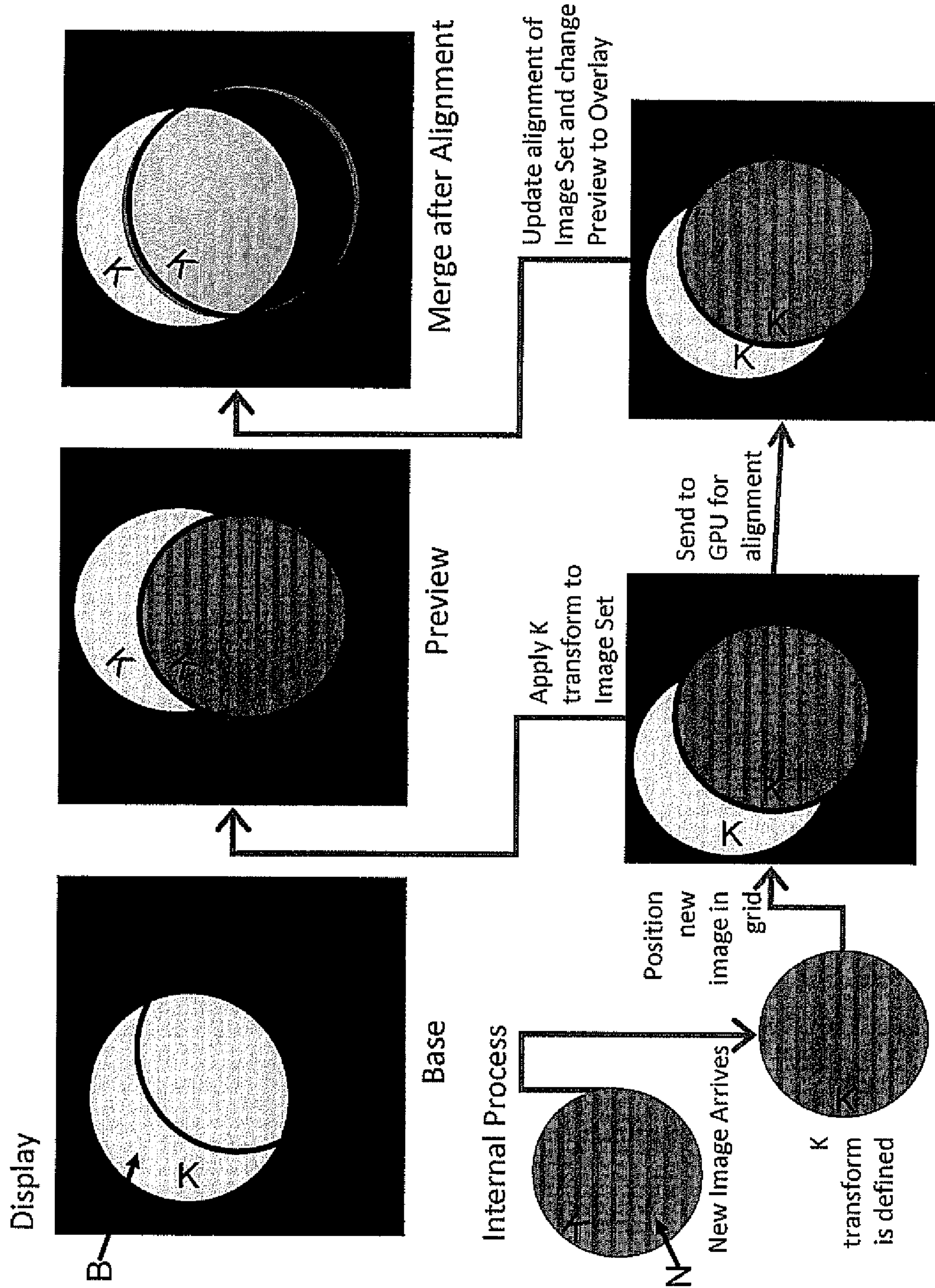
FIG. 11 is a graphical representation of an image alignment process according to the present disclosure.

In another approach, the image recognition or registration step 210 may include steps to measure the similarity of the LD image to a transformed version of the baseline image (i.e., a baseline image that has been transformed to account for movement of the C-arm, as described below relative to FIG. 11) or of the patient. In an image-guided surgical procedure, the C-arm system acquires multiple X-ray images of the same anatomy. Over the course of this series of images the system may move in small increments and surgical tools may be added or removed from the field of view, even though the anatomical features may remain relatively stable. The approach described below takes advantage of this consistency in the anatomical features by using the anatomical features present in one image to fill in the missing details in another later image. This approach further allows the transfer of the high quality of a full dose image to subsequent low dose images.

In the present approach, a similarity function in the form of a scalar function of the images is used to determine the registration between a current LD image and a baseline image. To determine this registration it is first necessary to determine the incremental motion that has occurred between images. This motion can be described by four numbers corresponding to four degrees of freedom—scale, rotation and vertical and horizontal translation. For a given pair of images to be compared knowledge of these four numbers allows one of the images to be manipulated so that the same anatomical features appear in the same location between both images. The scalar function is a measure of this registration and may be obtained using a correlation coefficient, dot product or mean square error. By way of example, the dot product scalar function corresponds to the sum of the products of the intensity values at each pixel pair in the two images. For example, the intensity values for the pixel located at 1234, 1234 in each of the LD and baseline images are multiplied. A similar calculation is made for every other pixel location and all of those multiplied values are added for the scalar function. It can be appreciated that when two images are in exact registration this dot product will have the maximum possible magnitude. In other words, when the best combination is found, the corresponding dot product it typically higher than the others, which may be reported as the Z score (i.e., number of standard deviations above the mean). A Z score greater than 7.5 represents a 99.9999999% certainty that the registration was not found by chance. It should be borne in mind that the registration being sought using this dot product is between a baseline image of a patient's anatomy and a real-time low dose image of that same anatomy taken at a later time after the viewing field and imaging equipment may have moved or non-anatomical objects introduced into the viewing field.

This approach is particularly suited to performance using a parallel computing architecture such as the GPU which consists of multiple processors capable of performing the same computation in parallel. Each processor of the GPU may thus be used to compute the similarity function of the LD image and one transformed version of the baseline image. In this way, multiple transformed versions of the baseline image can be compared to the LD image simultaneously. The transformed baseline images can be generated in advance when the baseline is acquired and then stored in GPU memory. Alternatively, a single baseline image can be stored and transformed on the fly during the comparison by reading from transformed coordinates with texture fetching. In situations in which the number of processors of the GPU greatly exceeds the number of transformations to be considered, the baseline image and the LD image can be broken into different sections and the similarity functions for each section can be computed on different processors and then subsequently merged.

To further accelerate the determination of the best transformation to align two images, the similarity functions can first be computed with down-sampled images that contain fewer pixels. This down-sampling can be performed in advance by averaging together groups of neighboring pixels. The similarity functions for many transformations over a broad range of possible motions can be computed for the down-sampled images first. Once the best transformation from this set is determined that transformation can be used as the center for a finer grid of possible transformations applied to images with more pixels. In this way, multiple steps are used to determine the best transformation with high precision while considering a wide range of possible transformations in a short amount of time.

In order to reduce the bias to the similarity function caused by differences in the overall intensity levels in the different images, and to preferentially align anatomical features in the images that are of interest to the user, the images can be filtered before the similarity function is computed. Such filters will ideally suppress the very high spatial frequency noise associated with low dose images, while also suppressing the low spatial frequency information associated with large, flat regions that lack important anatomical details. This image filtration can be accomplished with convolution, multiplication in the Fourier domain or Butterworth filters, for example. It is thus contemplated that both the LD image and the baseline image(s) will be filtered accordingly prior to generating the similarity function.

As previously explained, non-anatomical features may be present in the image, such as surgical tools, in which case modifications to the similarity function computation process may be necessary to ensure that only anatomical features are used to determine the alignment between LD and baseline images. A mask image can be generated that identifies whether or not a pixel is part of an anatomical feature. In one aspect, an anatomical pixel may be assigned a value of 1 while a non-anatomical pixel is assigned a value of 0. This assignment of values allows both the baseline image and the LD image to be multiplied by the corresponding mask images before the similarity function is computed as described above In other words, the mask image can eliminate the non-anatomical pixels to avoid any impact on the similarity function calculations.

To determine whether or not a pixel is anatomical, a variety of functions can be calculated in the neighborhood around each pixel. These functions of the neighborhood may include the standard deviation, the magnitude of the gradient, and/or the corresponding values of the pixel in the original grayscale image and in the filtered image. The "neighborhood" around a pixel includes a pre-determined number of adjacent pixels, such as a 5×5 or a 3×3 grid. Additionally, these functions can be compounded, for example, by finding the standard deviation of the neighborhood of the standard deviations, or by computing a quadratic function of the standard deviation and the magnitude of the gradient. One example of a suitable function of the neighborhood is the use of edge detection techniques to distinguish between bone and metallic instruments. Metal presents a "sharper" edge than bone and this difference can be determined using standard deviation or gradient calculations in the neighborhood of an "edge" pixel. The neighborhood functions may thus determine whether a pixel is anatomic or non-anatomic based on this edge detection approach and assign a value of 1 or 0 as appropriate to the pixel.

Once a set of values has been computed for the particular pixel, the values can be compared against thresholds determined from measurements of previously-acquired images and a binary value can be assigned to the pixel based on the number of thresholds that are exceeded. Alternatively, a fractional value between 0 and 1 may be assigned to the pixel, reflecting a degree of certainty about the identity of the pixel as part of an anatomic or non-anatomic feature. These steps can be accelerated with a GPU by assigning the computations at one pixel in the image to one processor on the GPU, thereby enabling values for multiple pixels to be computed simultaneously. The masks can be manipulated to fill in and expand regions that correspond to non-anatomical features using combinations of morphological image operations such as erosion and dilation.

Figure 4A:
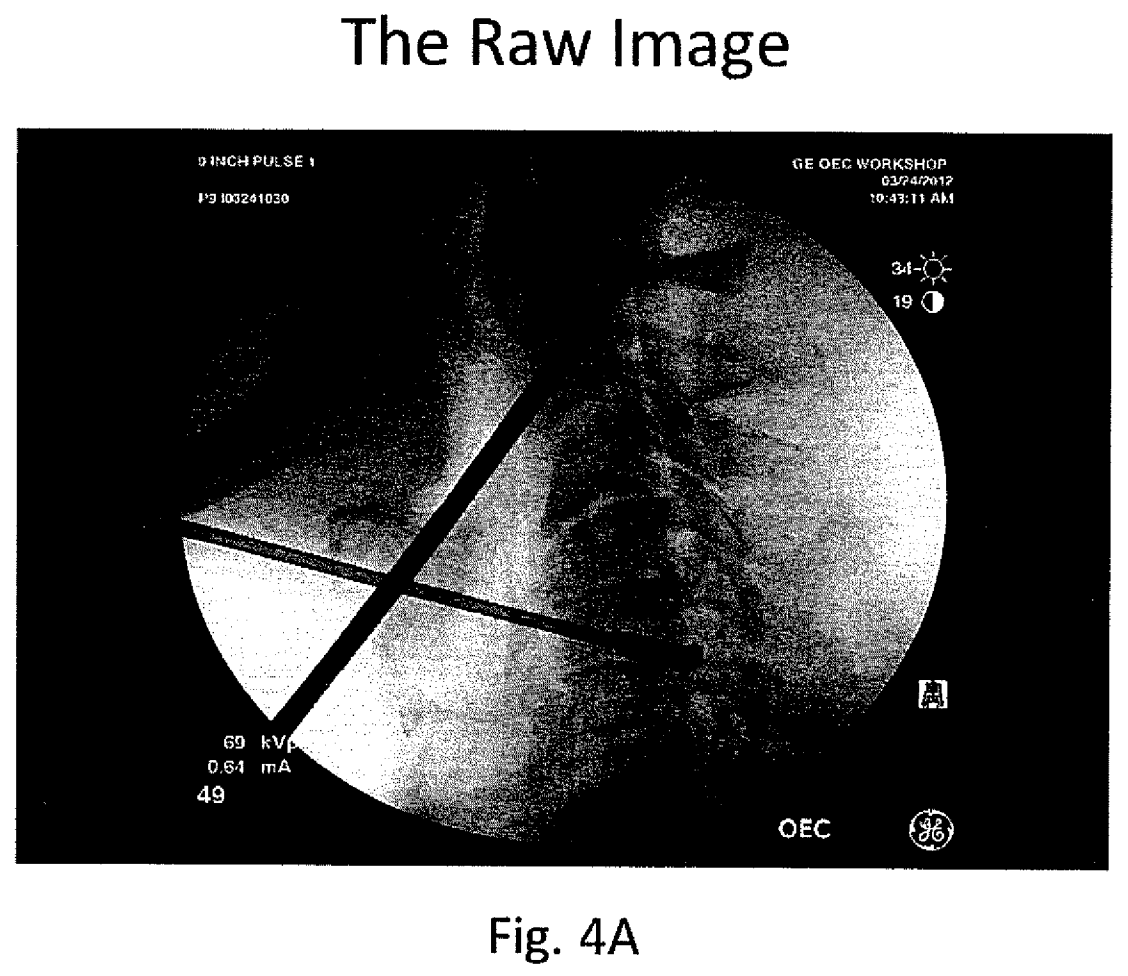
Figure 4B:
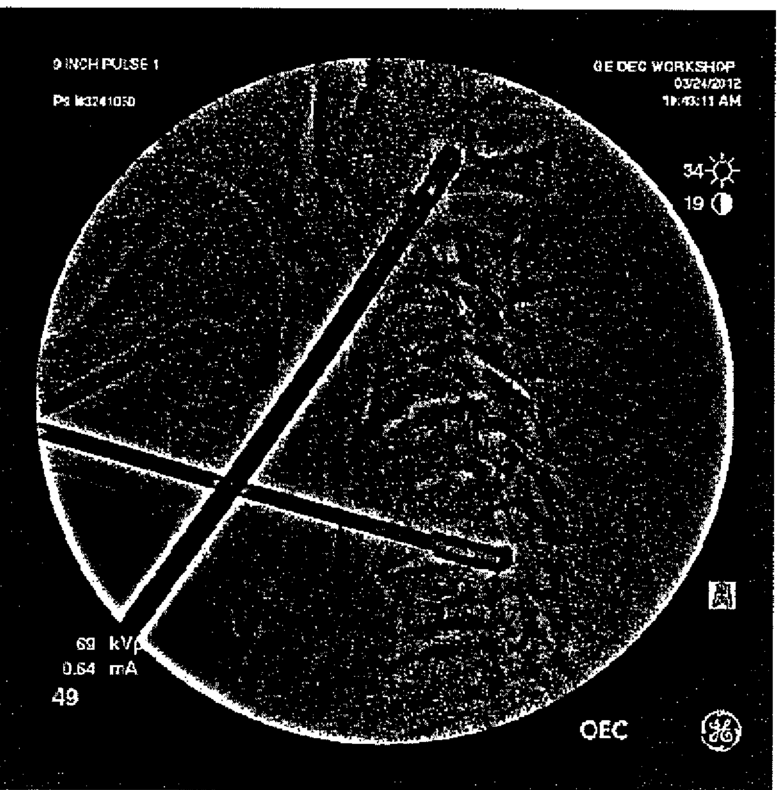
FIG. 4B is an image of the surgical field shown in FIG. 4A with edge enhancement.
Figure 4C:
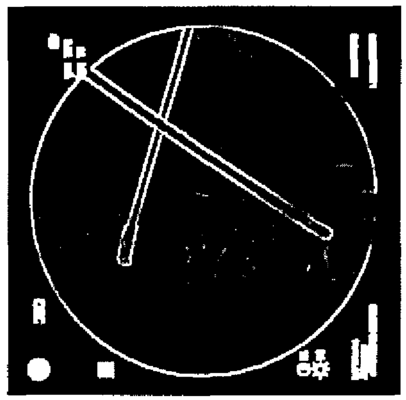
FIG. 4C, FIG. 4D, FIG. 4E, FIG. 4F, FIG. 4G, FIG. 4H, FIG. 4I, and FIG. 4J are images showing the surgical field of FIG. 4B with different functions applied to determine the anatomic and non-anatomic features in the view.
Figure 4D:
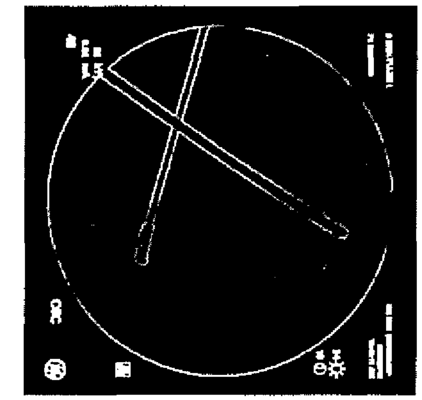
Figure 4E:
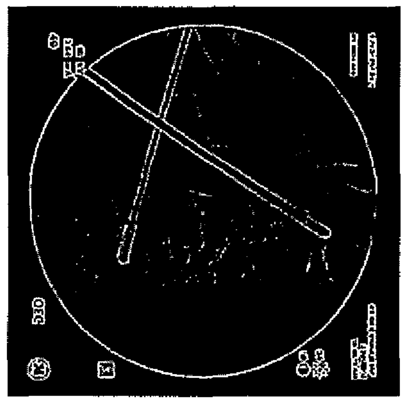
Figure 4F:
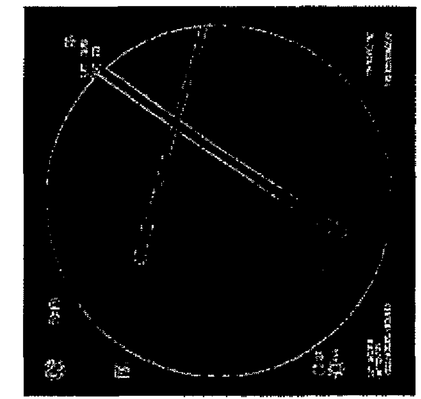
Figure 4G:
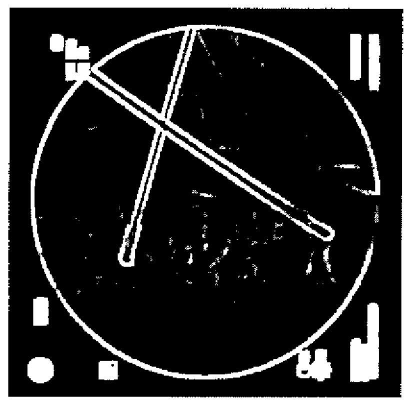
Figure 4H:
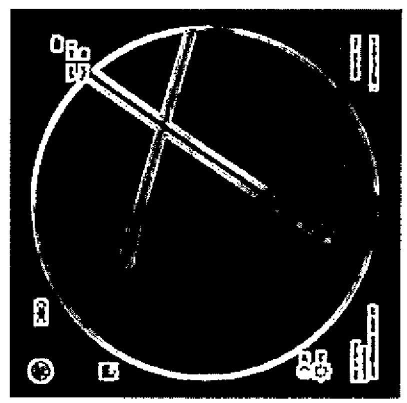
Figure 4I:
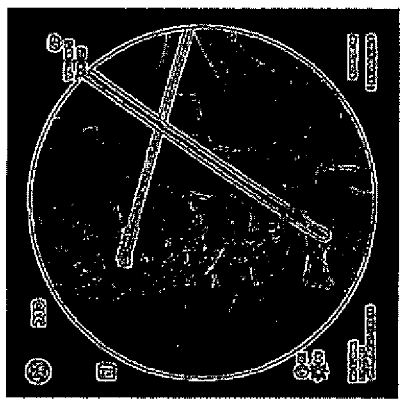
Figure 4J:
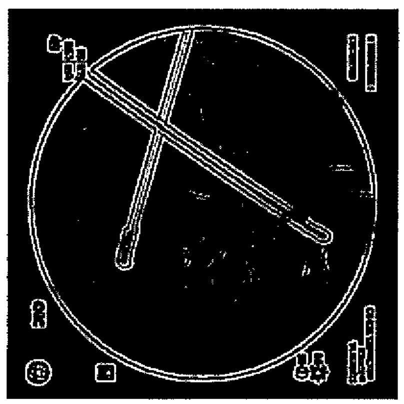
Figure 4L:
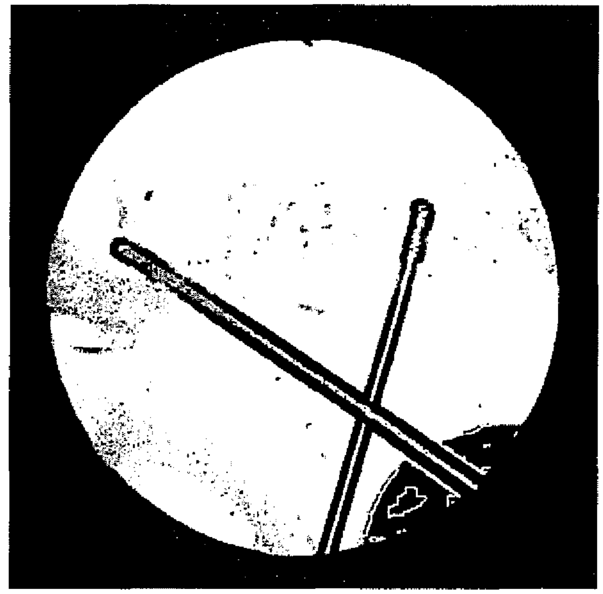
FIG. 4K and FIG. 4L are images of a mask generated using a threshold and a table lookup.
Figure 4K:
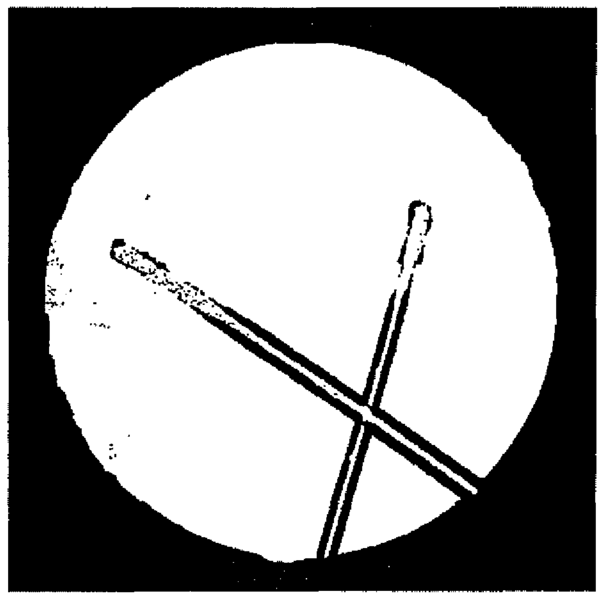
Figure 4N:
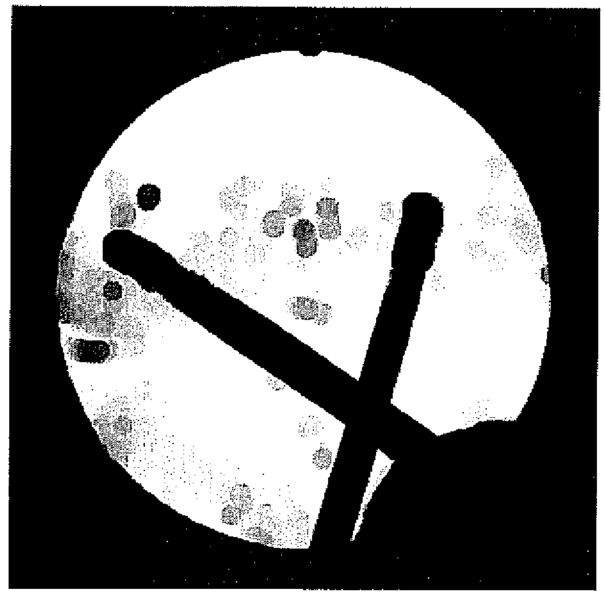
FIG. 4M and FIG. 4N are images of the masks shown in FIG. 4K and FIG. 4L, respectively, after dilation and erosion.
Figure 4M:
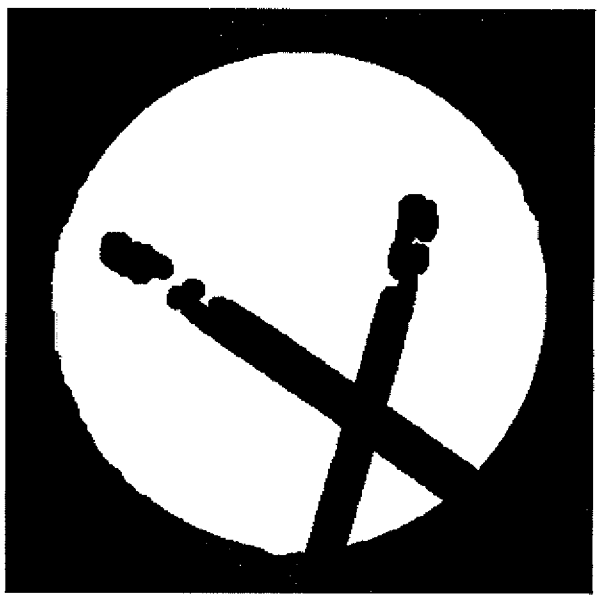
Figure 4O:
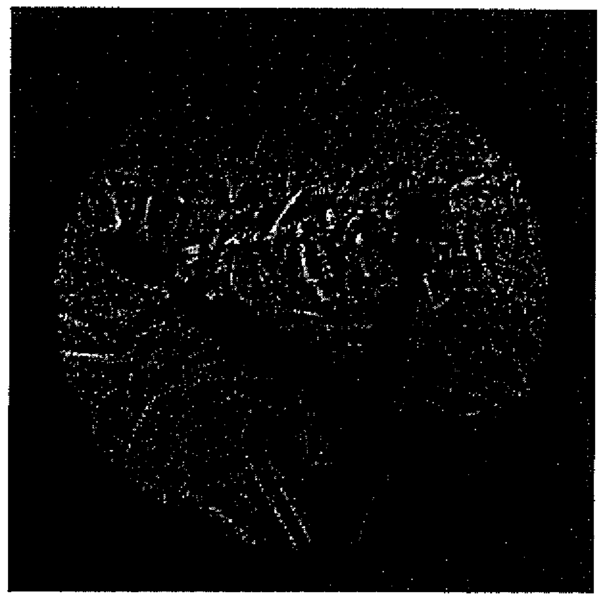
FIG. 4O and FIG. 4P are images prepared by applying the masks of FIG. 4M and FIG. 4N, respectively, to the filter image of FIG. 4B to eliminate the non-anatomic features from the image.
Figure 4P:
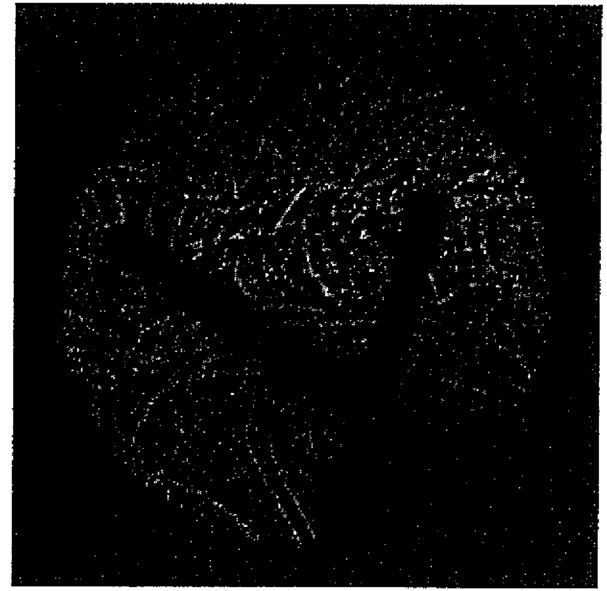

An example of the steps of this approach is illustrated in the images of FIGS. 4A-4P. In FIG. 4A, an image of a surgical site includes anatomic features (the patient's skull) and non-anatomic features (such as a clamp). The image of FIG. 4A is filtered for edge enhancement to produce the filtered image of FIG. 4B. It can be appreciated that this image is represented by thousands of pixels in a conventional manner, with the intensity value of each pixel modified according to the edge enhancement attributes of the filter. In this example, the filter is a Butterworth filter. This filtered image is then subject to eight different techniques for generating a mask corresponding to the non-anatomic features. Thus, the neighborhood functions described above (namely, standard deviation, gradient and compounded functions thereof) are applied to the filtered image FIG. 4B to produce different images FIGS. 4C-4J. Each of these images is stored as a baseline image for comparison to and registration with a live LD image.

Thus, each image of FIGS. 4C-4J is used to generate a mask. As explained above, the mask generation process may be by comparison of the pixel intensities to a threshold value or by a lookup table in which intensity values corresponding to known non-anatomic features is compared to the pixel intensity. The masks generated by the threshold and lookup table techniques for one of the neighborhood function images is shown in FIGS. 4K-4L. The masks can then be manipulated to fill in and expand regions that correspond to the non-anatomical features, as represented in the images of FIGS. 4M-4N. The resulting mask is then applied to the filtered image of FIG. 4B to produce the "final" baseline images of FIGS. 4O-4P that will be compared to the live LD image. As explained above, each of these calculations and pixel evaluations can be performed in the individual processors of the GPU so that all of these images can be generated in an extremely short time. Moreover, each of these masked baseline images can be transformed to account for movement of the surgical field or imaging device and compared to the live LD image to find the baseline image that yields the highest Z score corresponding to the best alignment between baseline and LD images. This selected baseline image is then used in manner explained below.

Figures 5A, 5B:
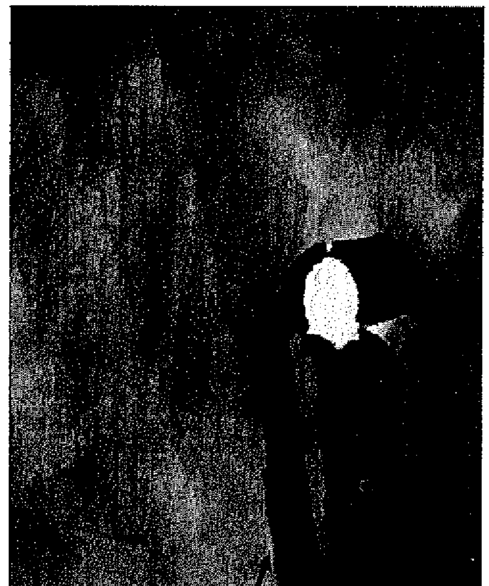
FIG. 5A is an image of a surgical field including an object blocking a portion of the anatomy.
FIG. 5B is an image of the surgical field shown in FIG. 5A with the image of FIG. 5A partially merged with a baseline image to display the blocked anatomy.
Figures 6A, 6B:
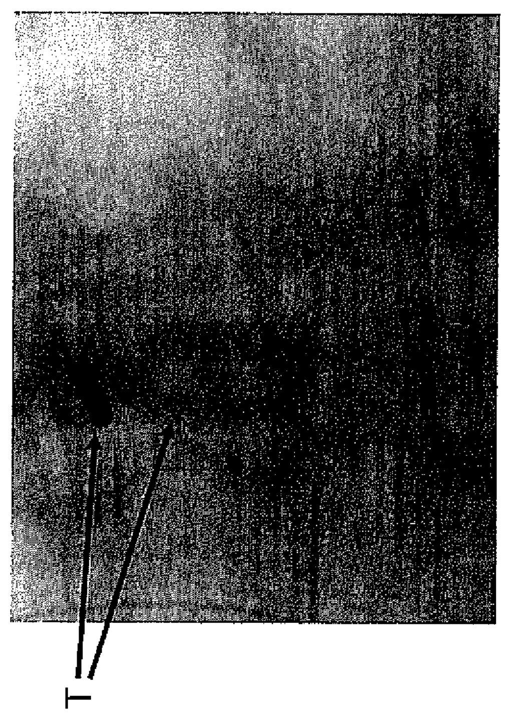
FIG. 6A and FIG. 6B are baseline and merged images of a surgical field including a blocking object.

Once the image registration is complete, the new image may be displayed with the selected image from the baseline image set in different ways. In one approach, the two images are merged, as illustrated in FIGS. 5A, 5B. The original new image is shown in FIG. 5A with the instrument T plainly visible and blocking the underlying anatomy. A partially merged image generated in step 212 (FIG. 3) is shown in FIG. 5B in which the instrument T is still visible but substantially mitigated and the underlying anatomy is visible. The two images may be merged by combining the digital representation of the images in a conventional manner, such as by adding or averaging pixel data for the two images. In one embodiment, the surgeon may identify one or more specific regions of interest in the displayed image, such as through the user interface 125, and the merging operation can be configured to utilize the baseline image data for the display outside the region of interest and conduct the merging operation for the display within the region of interest. The user interface 125 may be provided with a "slider" that controls the amount the baseline image versus the new image that is displayed in the merged image. In another approach, the surgeon may alternate between the correlated baseline image and the new image or merged image, as shown in FIGS. 6A, 6B. The image in FIG. 6A is the image from the baseline image set found to have the highest degree of correlation to the new image. The image in FIG. 6B is the new image obtained. The surgeon may alternate between these views to get a clearer view of the underlying anatomy and a view of the current field with the instrumentation T, which in effect by alternating images digitally removes the instrument from the field of view, clarifying its location relative to the anatomy blocked by it.

In another approach, a logarithmic subtraction can be performed between the baseline image and the new image to identify the differences between the two images. The resulting difference image (which may contain tools or injected contrast agent that are of interest to the surgeon) can be displayed separately, overlaid in color or added to the baseline image, the new image or the merged image so that the features of interest appear more obvious. This may require the image intensity values to be scaled prior to subtraction to account for variations in the C-arm exposure settings. Digital image processing operations such as erosion and dilation can be used to remove features in the difference image that correspond to image noise rather than physical objects. The approach may be used to enhance the image differences, as described, or to remove the difference image from the merged image. In other words, the difference image may be used as a tool for exclusion or inclusion of the difference image in the baseline, new or merged images.

As described above, the image enhancement system of the present disclosure can be used to minimize radio-opaque instruments and allow visualization of anatomy underlying the instrumentation. Alternatively, the present system can be operable to enhance selected instrumentation in an image or collection of images. In particular, the masks describe above used to identify the location of the non-anatomic features can be selectively enhanced in an image. The same data can also be alternately manipulated to enhance the anatomic features and the selected instrumentation. This feature can be used to allow the surgeon to confirm that the visualized landscape looks as expected, to help identify possible distortions in the image, and to assist in image guided instrumentation procedures. Since the bone screw is radio-opaque it can be easily visualized under a very low dose x-ray a low dose new image can be used to identify the location of the instrumentation while merged with the high dose baseline anatomy image. Multiple very low dose images can be acquired as the bone screw is advanced into the bone to verify the proper positioning of the bone screw. Since the geometry of the instrument, such as the bone screw, is known (or can be obtained or derived such as from image guidance, 2-D projection or both), the pixel data used to represent the instrument in the x-ray image can be replaced with a CAD model mapped onto the edge enhanced image of the instrument.

As indicated above, the present invention also contemplates a surgical navigation procedure in which the imaging device or C-arm 103 is moved. Thus, the present invention contemplates tracking the position of the C-arm rather than tracking the position of the surgical instruments and implants as in traditional surgical navigation techniques, using commercially available tracking devices or the DICOM information from the imaging device. Tracking the C-arm requires a degree of accuracy that is much less than the accuracy required to track the instruments and implants. In this embodiment, the image processing device 122 receives tracking information from the tracking device 130. The object of this aspect of the invention is to ensure that the surgeon sees an image that is consistent with the actual surgical site regardless of the orientation of the C-arm relative to the patient.

Tracking the position of the C-arm can account for "drift", which is a gradual misalignment of the physical space and the imaging (or virtual) space. This "drift" can occur because of subtle patient movements, inadvertent contact with the table or imaging device and even gravity. This misalignment is often visually imperceptible, but can generate noticeable shifts in the image viewed by the surgeon. These shifts can be problematic when the surgical navigation procedure is being performed (and a physician is relying on the information obtained from this device) or when alignment of new to baseline images is required to improve image clarity. The use of image processing eliminates the inevitable misalignment of baseline and new images. The image processing device 122 further may incorporate a calibration mode in which the current image of the anatomy is compared to the predicted image. The difference between the predicted and actual movement of the image can be accounted for by an inaccurate knowledge of the "center of mass" or COM, described below, and drift. Once a few images are obtained and the COM is accurately established, recalibration of the system can occur automatically with each successive image taken and thereby eliminating the impact of drift.

Figures 7A, 7B:
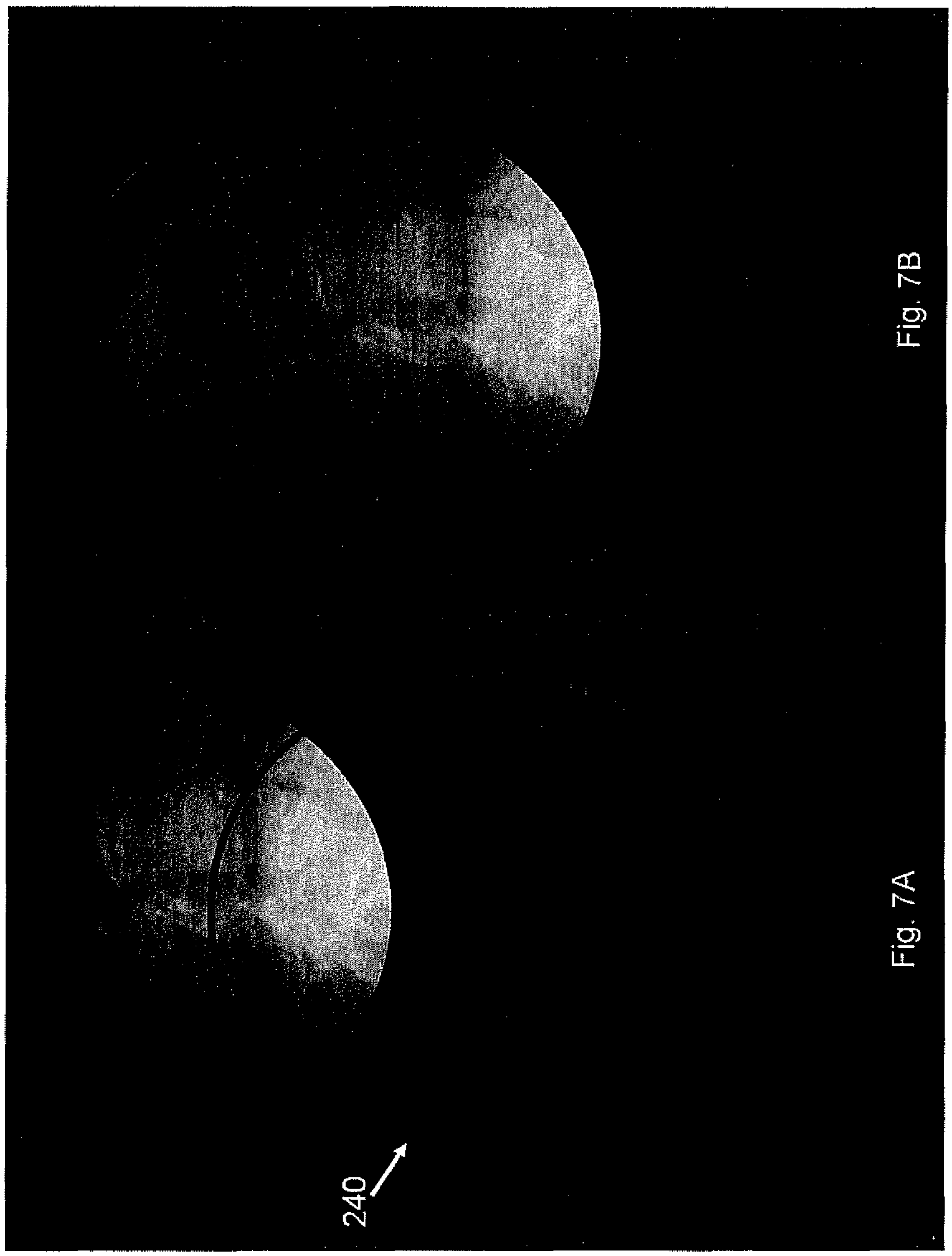
FIG. 7A and FIG. 7B are displays of the surgical field adjusted for movement of the imaging device or C-arm and providing an indicator of an in-bounds or out-of-bounds position of the imaging device for acquiring a new image.
Figures 8A, 8B:
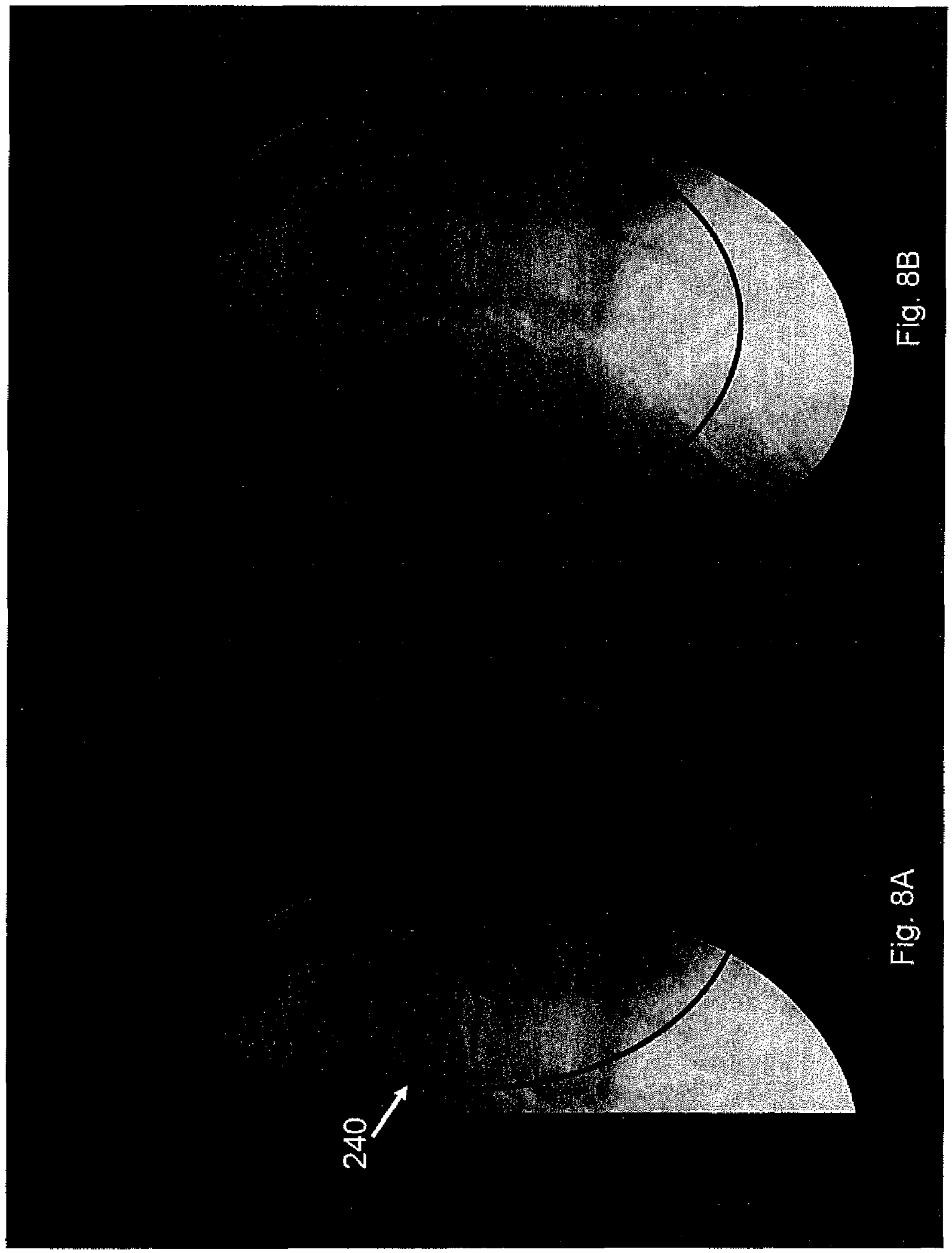
FIG. 8A and FIG. 8B are displays of the surgical field adjusted for movement of the imaging device or C-arm and providing an indicator of when a new image can be stitched to a previously acquired image.

The image processing device 122 may operate in a "tracking mode" in which the movement of the C-arm is monitored and the currently displayed image is moved accordingly. The currently displayed image may be the most recent baseline image, a new LD image or a merged image generated as described above. This image remains on one of the displays 123, 124 until a new picture is taken by the imaging device 100. This image is shifted on the display to match the movement of the C-arm using the position data acquired by the tracking device 130. A tracking circle 240 may be shown on the display, as depicted in FIGS. 7A, 7B. The tracking circle identifies an "in bounds" location for the image. When the tracking circle appears in red, the image that would be obtained with the current C-arm position would be "out of bounds" in relation to a baseline image position, as shown in FIG. 7A. As the C-arm is moved by the radiology technician the representative image on the display is moved. When the image moves "in bounds", as shown in FIG. 7B, the tracking circle 240 turns green so that the technician has an immediate indication that the C-arm is now in a proper position for obtaining a new image. The tracking circle may be used by the technician to guide the movements of the C-arm during the surgical procedure. The tracking circle may also be used to assist the technician in preparing a baseline stitched image. Thus, an image position that is not properly aligned for stitching to another image, as depicted in FIG. 8A, will have a red tracking circle 240, while a properly aligned image position, as shown in FIG. 8B, will have a green tracking circle. The technician can then acquire the image to form part of the baseline stitched image.

The tracking circle 240 may include indicia on the circumference of the circle indicative of the roll position of the C-arm in the baseline image. A second indicia, such as an arrow, may also be displayed on the circumference of the tracking circle in which the second indicia rotates around the tracking circle with the roll movement of the C-arm. Alignment of the first and second indicia corresponds to alignment of the roll degree of freedom between the new and baseline images.

In many instances an x-ray image is taken at an angle to avoid certain anatomical structures or to provide the best image of a target. In these instances, the C-arm is canted or pitched to find the best orientation for the baseline image. It is therefore desirable to match the new image to the baseline image in six degrees of freedom—X and Y translations, Z translation corresponding to scaling (i.e., closer or farther away from the target), roll or rotation about the Z axis, and pitch and yaw (rotation about the X and Y axes, respectively). Aligning the view finder in the X, Y, Z and roll directions can be indicated by the color of the tracking circle, as described above. It can be appreciated that using the view finder image appearing on the display four degrees of freedom of movement can be readily visualized, namely X and Y translation, zoom or Z translation and roll about the Z-axis. However, it is more difficult to directly visualize movement in the other two degrees of freedom—pitch and yaw—on the image display. Aligning the tracking circle 240 in the pitch and yaw requires a bit more complicated movement of the C-arm and the view finder associated with the C-arm. In order to facilitate this movement and alignment, a vertical slider bar corresponding to the pitch movement and a horizontal slider bar corresponding to the yaw movement can be shown on the display. The new image is properly located when indicators along the two slider bars are centered. The slider bars can be in red when the new image is misaligned relative to the baseline image in the pitch and yaw degrees of freedom, and can turn green when properly centered. Once all of the degrees of freedom have been aligned with the X, Y, Z, roll, pitch and yaw orientations of the original baseline image, the technician can take the new image and the surgeon can be assured that an accurate and meaningful comparison can be made between the new image and the baseline image.

Figure 8C:
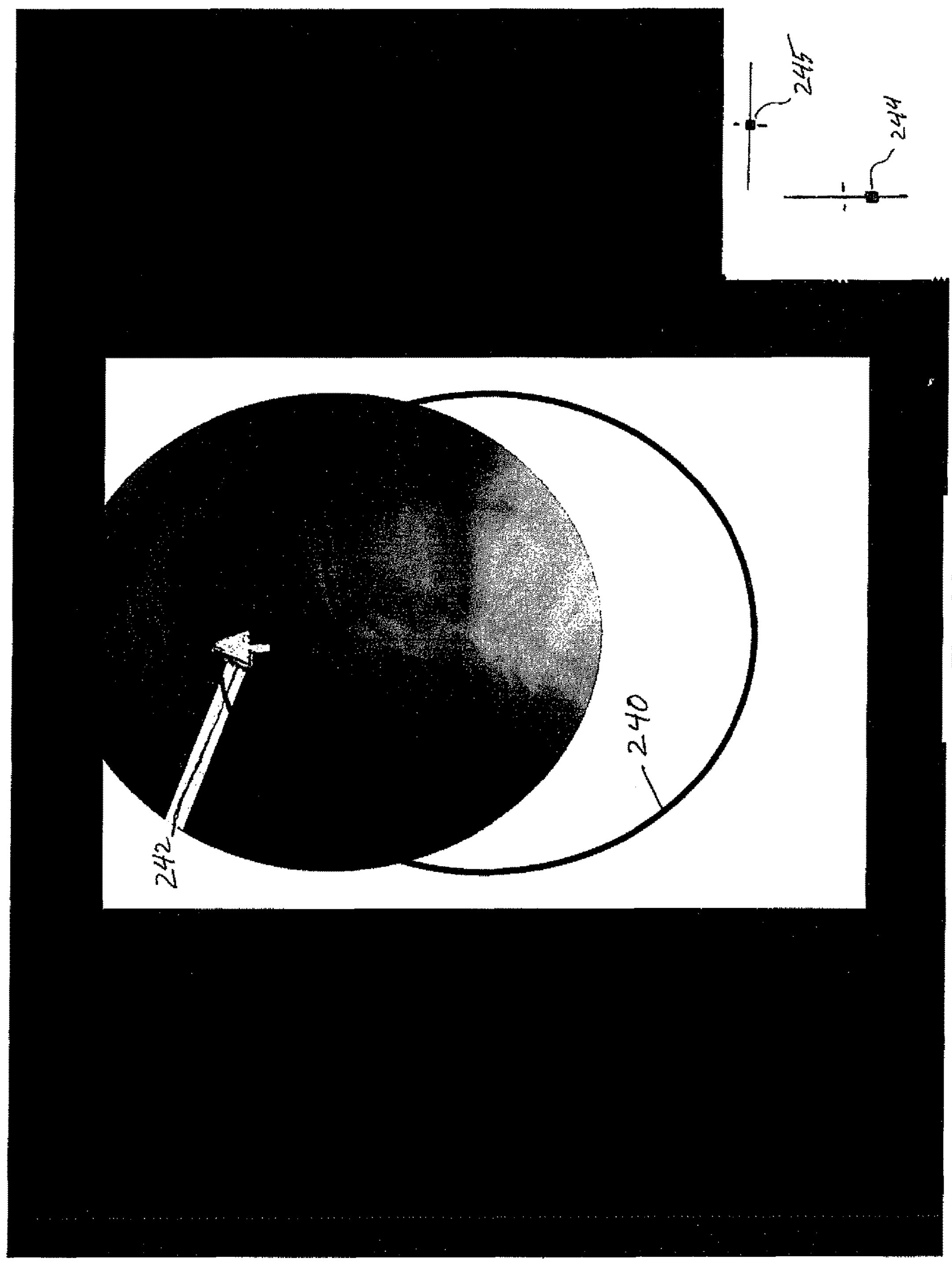
FIG. 8C is a screen print of a display showing a baseline image with a tracking circle and direction of movement indicator for use in orienting the C-arm for acquiring a new image.

The spatial position of the baseline image is known from the 6DOF position information obtained when the baseline image was generated. This 6DOF position information includes the data from the tracking device 130 as well as any angular orientation information obtained from the C-arm itself. When it is desired to generate a new image at the same spatial position as the baseline image, new spatial position information is being generated as the C-arm is moved. Whether the C-arm is aligned with the baseline image position can be readily ascertained by comparing the 6DOF position data, as described above. In addition, this comparison can be used to provide an indication to the radiology technician as to how the C-arm needs to be moved to obtain proper alignment. In other words, if the comparison of baseline position data to current position data shows that the C-arm is misaligned to the left, an indication can be provided directing the technician to move the C-arm to the right. This indication can be in the form of a direction arrow 242 that travels around the tracking circle 240, as depicted in the screen shot of FIG. 8C. The direction of movement indicator 242 can be transformed to a coordinate system corresponding to the physical position of the C-arm relative to the technician. In other words, the movement indicator 242 points vertically upward on the image in FIG. 8C to indicate that the technician needs to move the C-arm upward to align the current image with the baseline image. As an alternative to the direction arrow 242 on the tracking circle, the movement direction may be indicated on perpendicular slider bars adjacent to the image, such as the bars 244, 245 in FIG. 8C. The slider bars can provide a direct visual indication to the technician of the offset of the bar from the centered position on each bar. In the example of FIG. 8C the vertical slider bar 244 is below the centered position so the technician immediately knows to move the C-arm vertically upward.

Figure 8D:
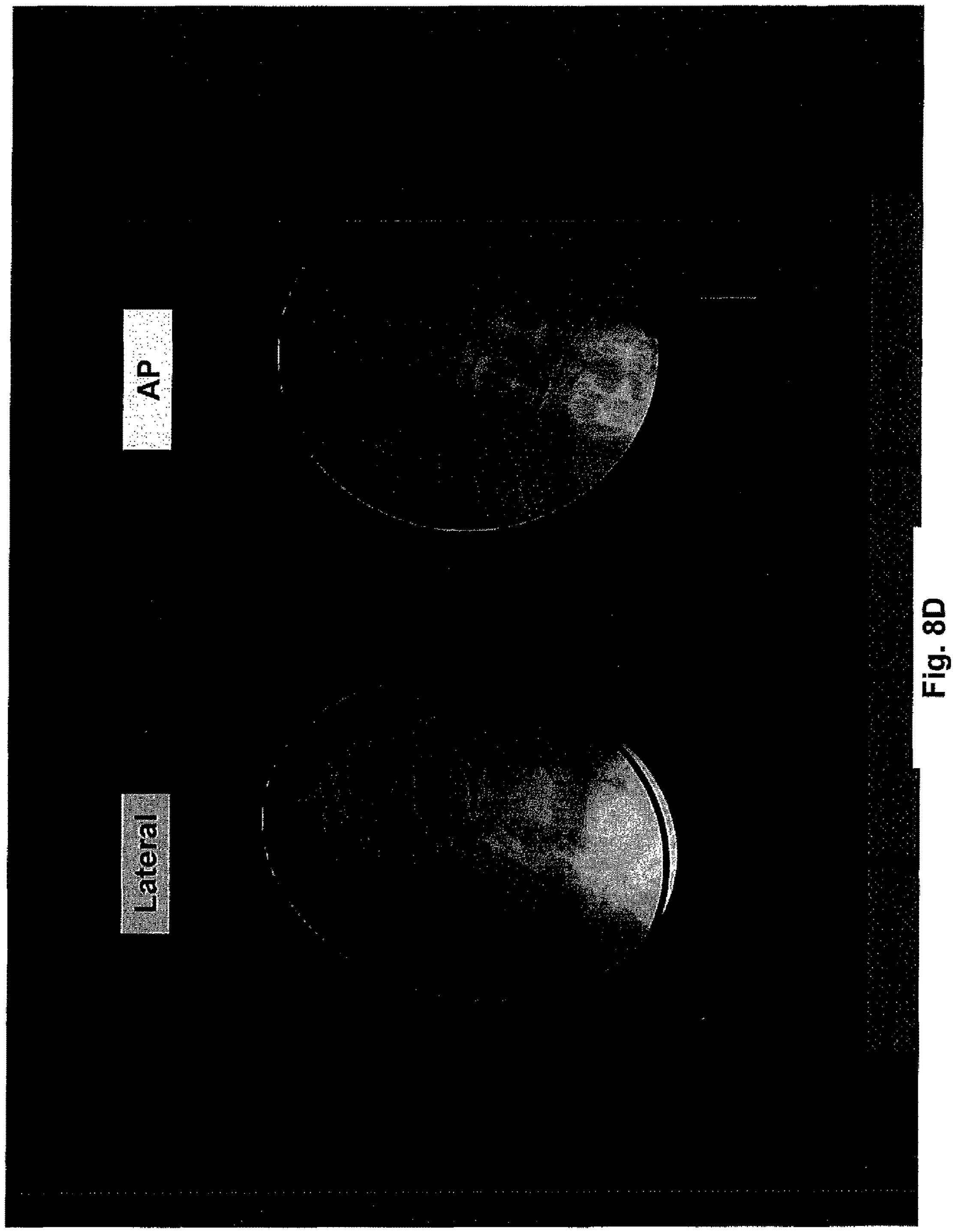
FIG. 8D is a screen shot of a display of a two view finder used to assist in orienting the imaging device or C-arm to obtain a new image at the same spatial orientation as a baseline image.

In a further embodiment, two view finder images can be utilized by the radiology technician to orient the C-arm to acquire a new image at the same orientation as a baseline image. In this embodiment, the two view finder images are orthogonal images, such as an anterior-posterior (AP) image (passing through the body from front to back) and a lateral (LAT) image (passing through the body shoulder to shoulder), as depicted in the screen shot of FIG. 8D. The technician seeks to align both view finder images to corresponding AP and LAT baseline images. As the C-arm is moved by the technician, both images are tracked simultaneously, similar to the single view finder described above. Each view finder incorporates a tracking circle which responds in the manner described above—i.e., red for out of bounds and green for in bounds. The technician to switch between the AP and LAT viewfinders as the C-arm is manipulated. Once the tracking circle is within a predetermined range of proper alignment, the display can switch from the two view finder arrangement to the single view finder arrangement described above to help the technician to fine tune the position of the C-arm.

It can be appreciated that the two view navigation images may be derived from a baseline image and a single shot or X-ray image at a current position, such as a single AP image. In this embodiment, the lateral image is a projection of the AP image as if the C-arm was actually rotated to a position to obtain the lateral image. As the view finder for the AP image is moved to position the view at a desired location, the second view finder image displays the projection of that image in the orthogonal plane (i.e., the lateral view). The physician and x-ray technician can thus maneuver the C-arm to the desired location for a lateral view based on the projection of the original AP view. Once the C-arm is aligned with the desired location, the C-arm can then actually be positioned to obtain the orthogonal (i.e., lateral) x-ray image.

In the discussion above, the tracking function of the imaging system disclosed herein is used to return the C-arm to the spatial position at which the original baseline image was obtained. The technician can acquire a new image at the same location so that the surgeon can compare the current image to the baseline image. Alternatively, this tracking function can be used by the radiology technician to acquire a new image at a different orientation or at an offset location from the location of a baseline image. For instance, if the baseline image was an AP view of the L3 vertebra and it is desired to obtain an image a specific feature of that vertebra, the tracking feature can be used to quickly guide the technician to the vertebra and then to the desired alignment over the feature of interest. The tracking feature of the present invention thus allows the technician to find the proper position for the new image without having to acquire intermediate images to verify the position of the C-arm relative to the desired view.

The image tracking feature can also be used when stitching multiple images, such as to form a complete image of a patient's spine. As indicated above, the tracking circle 240 depicts the location of the C-arm relative to the anatomy as if an image were taken at that location and orientation. The baseline image (or some selected prior image) also appears on the display with the tracking circle offset from the baseline image indicative of the offset of the C-arm from the position at which the displayed image was taken. The position of the tracking circle relative to the displayed baseline image can thus be adjusted to provide a degree of overlap between the baseline image and a new image taken at the location of the tracking circle. Once a C-arm has been moved to a desired overlap, the new image can be taken. This new image is then displayed on the screen along with the baseline image as the two images are stitched together. The tracking circle is also visible on the display and can be used to guide movement of the C-arm for another image to be stitched to the other two images of the patient's anatomy. This sequence can be continued until all of the desired anatomy has been imaged and stitched together.

Figures 9A, 9B:
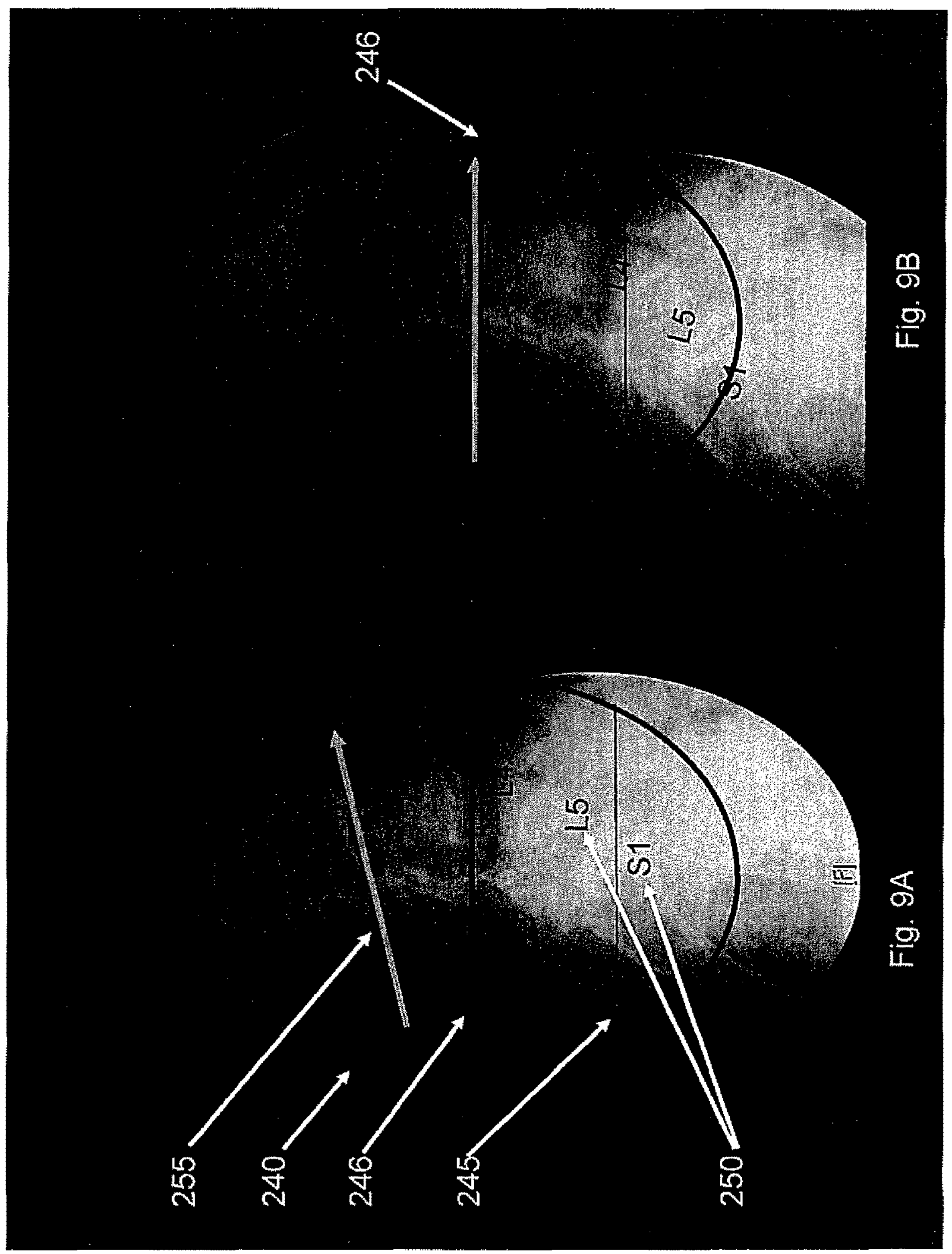
FIG. 9A and FIG. 9B are displays of the surgical field adjusted for movement of the imaging device or C-arm and providing an indicator of alignment of the imaging device with a desired trajectory for acquiring a new image.

The present invention contemplates a feature that enhances the communication between the surgeon and the radiology technician. During the course of a procedure the surgeon may request images at particular locations or orientations. One example is what is known as a "Ferguson view" in spinal procedures in which an AP oriented C-arm is canted to align directly over a vertebral end plate with the end plate oriented "flat" or essentially parallel with the beam axis of the C-arm. Obtaining a Ferguson view requires rotating the C-arm or the patient table while obtaining multiple AP views of the spine, which is cumbersome and inaccurate using current techniques, requiring a number of fluoroscopic images to be performed to find the one best aligned to the endplate. The present invention allows the surgeon to overlay a grid onto a single image or stitched image and provide labels for anatomic features that can then be used by the technician to orient the C-arm. Thus, as shown in FIG. 9A, the image processing device 122 is configured to allow the surgeon to place a grid 245 within the tracking circle 240 overlaid onto a Lateral image. The surgeon may also locate labels 250 identifying anatomic structure, in this case spinal vertebrae. In this particular example, the goal is to align the L2-L3 disc space with the center grid line 246. To assist the technician, a trajectory arrow 255 is overlaid onto the image to indicate the trajectory of an image acquired with the C-arm in the current position. As the C-arm moves, changing orientation off of pure AP, the image processing device evaluates the C-arm position data obtained from the tracking device 230 to determine the new orientation for trajectory arrow 255. The trajectory arrow thus moves with the C-arm so that when it is aligned with the center grid line 246, as shown in FIG. 9B, the technician can shoot the image knowing that the C-arm is properly aligned to obtain a Ferguson view along the L3 endplate. Thus, monitoring the lateral view until it is rotated and centered along the center grid line allows the radiology technician to find the AP Ferguson angle without guessing and taking a number of incorrect images.

Figure 10:
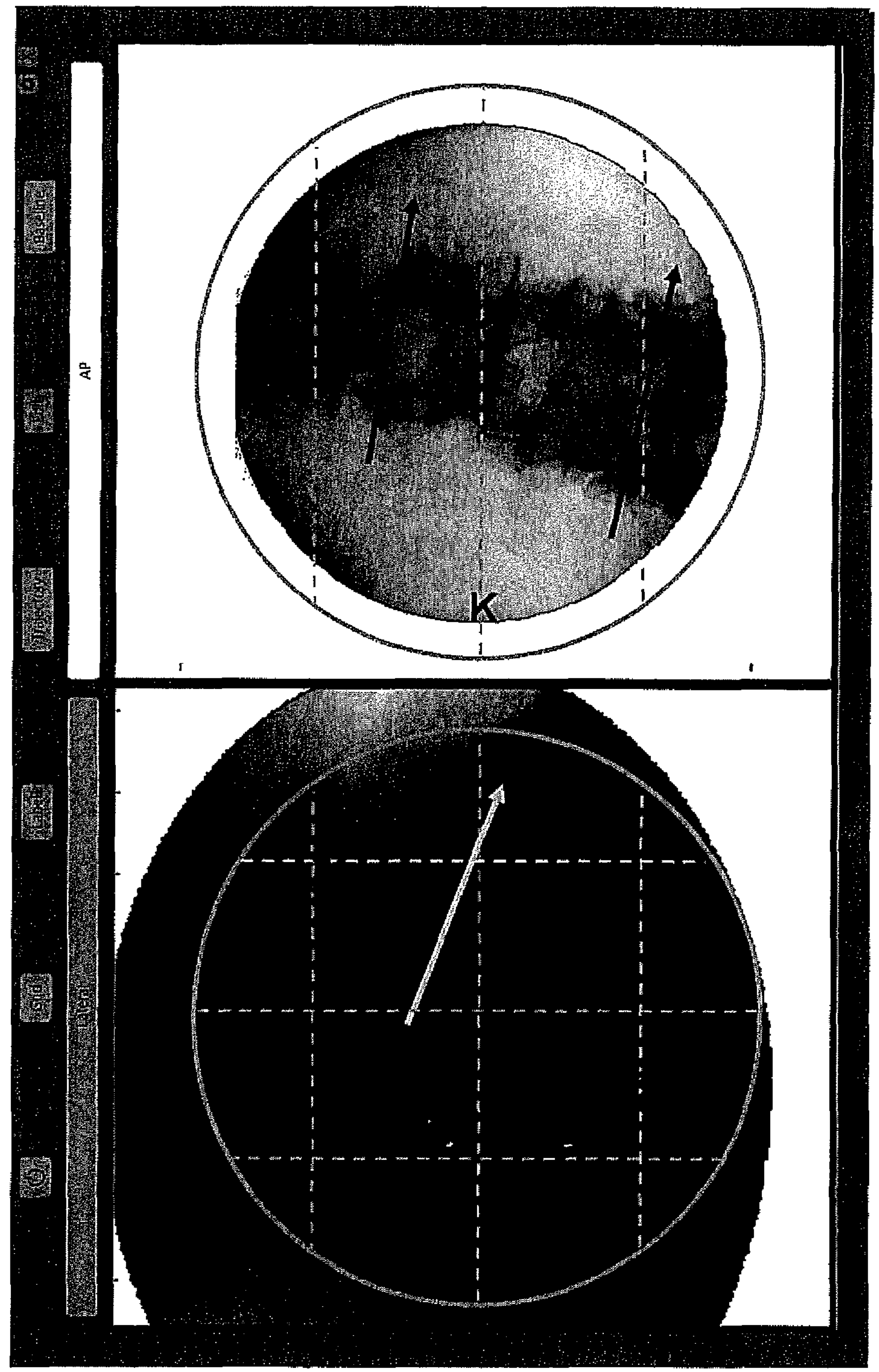
FIG. 10 is a depiction of a display and user interface for the image processing device shown in FIG. 1.

The image processing device may be further configured to show the lateral and AP views simultaneously on respective displays 123 and 124, as depicted in FIG. 10. Either or both views may incorporate the grid, labels and trajectory arrows. This same lateral view may appear on the control panel 110 for the imaging system 100 for viewing by the technician. As the C-arm is moved to align the trajectory arrow with the center grid line, as described above, both the lateral and AP images are moved accordingly so that the surgeon has an immediate perception of what the new image will look like. Again, once the technician properly orients the C-arm, as indicated by alignment of the trajectory arrow with the center grid line, a new AP image is acquired. As shown in FIG. 10, a view may include multiple trajectory arrows, each aligned with a particular disc space. For instance, the uppermost trajectory arrow is aligned with the L1-L2 disc space, while the lowermost arrow is aligned with the L5-S1 disc space. In multiple level procedures the surgeon may require a Ferguson view of different levels, which can be easily obtained by requesting the technician to align the C-arm with a particular trajectory arrow. The multiple trajectory arrows shown in FIG. 10 can be applied in a stitched image of a scoliotic spine and used to determine the Cobb angle. Changes in the Cobb angle can be determined live or interactively as correction is applied to the spine. A current stitched image of the corrected spine can be overlaid onto a baseline image or switched between the current and baseline images to provide a direct visual indication of the effect of the correction.

In another feature, a radiodense asymmetric shape or glyph can be placed in a known location on the C-arm detector. This creates the ability to link the coordinate frame of the C-arm to the arbitrary orientation of the C-arm's image coordinate frame. As the C-arm's display may be modified to generate an image having any rotation or mirroring, detecting this shape radically simplifies the process of image comparison and image stitching. Thus, as shown in FIG. 11, the baseline image B includes the indicia or glyph "K" at the 9 o'clock position of the image. In an alternative embodiment, the glyph may be in the form of an array of radio-opaque beads embedded in a radio-transparent component mounted to a C-arm collar, such as in a right triangular pattern. Since the physical orientation and location of the glyph relative to the C-arm is fixed, knowing the location and orientation of the glyph in a 2D image provides an automatic indication of the orientation of the image with respect to the physical world. The new image N is obtained in which the glyph has been rotated by the physician or technologist away from the default orientation. Comparing this new image to the baseline image set is unlikely to produce any registration between images due to this angular offset. In one embodiment, the image processing device detects the actual rotation of the C-arm from the baseline orientation while in another embodiment the image processing device uses image recognition software to locate the "K" glyph in the new image and determine the angular offset from the default position. This angular offset is used to alter the rotation and/or mirror image the baseline image set. The baseline image selected in the image registration step 210 is maintained in its transformed orientation to be merged with the newly acquired image. This transformation can include rotation and mirror-imaging, to eliminate the display effect that is present on a C-arm. The rotation and mirroring can be easily verified by the orientation of the glyph in the image. It is contemplated that the glyph, whether the "K" or the radio-opaque bead array, provides the physician with the ability to control the way that the image is displayed for navigation independent of the way that the image appears on the X-ray screen used by the technician. In other words, the imaging and navigation system disclosed herein allows the physician to rotate, mirror or otherwise manipulate the displayed image in a manner that physician wants to see while performing the procedure. The glyph provides a clear indication of the manner in which the image used by the physician has been manipulated in relation to the X-ray image. Once the physician's desired orientation of the displayed image has been set, the ensuing images retain that same orientation regardless of how the C-arm has been moved.

In another aspect, it is known that as the C-arm radiation source 104 moves closer to the table, the size of the image captured by the receiver 105 becomes larger; moving the receiver closer to the table results in a decrease in image size. Whereas the amount that the image scales with movements towards and away from the body can be easily determined, if the C-arm is translated along the table, the image will shift, with the magnitude of that change depending upon the proximity of the "center of mass" (COM) of the patient to the radiation source. Although the imaged anatomy is of 3D structures, with a high degree of accuracy, mathematically we can represent this anatomy as a 2D picture of the 3D anatomy placed at the COM of the structures. Then, for instance, when the COM is close to the radiation source, small movements will cause the resulting image to shift greatly. Until the COM is determined, though, the calculated amount that the objects on the screen shift will be proportional to but not equal to their actual movement. The difference is used to calculate the actual location of the COM. The COM is adjusted based on the amount that those differ, moving it away from the radiation source when the image shifted too much, and the opposite if the image shifts too little. The COM is initially assumed to be centered on the table to which the reference arc of the tracking device is attached. The true location of the COM is fairly accurately determined using the initial two or three images taken during initial set-up of the imaging system, and reconfirmed/adjusted with each new image taken. Once the COM is determined in global space, the movement of the C-arm relative to the COM can be calculated and applied to translate the baseline image set accordingly for image registration.

The image processing device 122 may also be configured to allow the surgeon to introduce other tracked elements into an image, to help guide the surgeon during the procedure. A closed-loop feedback approach allows the surgeon to confirm that the location of this perceived tracked element and the image taken of that element correspond. Specifically, the live x-ray and the determined position from the surgical navigation system are compared. In the same fashion that knowledge of the baseline image, through image recognition, can be used to track the patient's anatomy even if blocked by radiodense objects, knowledge of the radiodense objects, when the image taken is compared to their tracked location, can be used to confirm their tracking. When both the instrument/implant and the C-arm are tracked, the location of the anatomy relative to the imaging source and the location of the equipment relative to the imaging source are known. This information can thus be used to quickly and interactively ascertain the location of the equipment or hardware relative to the anatomy. This feature can, by way of example, have particular applicability to following the path of a catheter in an angio procedure, for instance. In a typical angio procedure, a cine, or continuous fluoro, is used to follow the travel of the catheter along a vessel. The present invention allows intersplicing previously generated images of the anatomy with the virtual depiction of the catheter with live fluoro shots of the anatomy and actual catheter. Thus, rather than taking 15 fluoro shots per second for a typical cine procedure, the present invention allows the radiology technician to take only one shot per second to effectively and accurately track the catheter as it travels along the vessel. The previously generated images are spliced in to account for the fluoro shots that are not taken. The virtual representations can be verified to the live shot when taken and recalibrated if necessary.

This same capability can be used to track instrumentation in image-guided or robotic surgeries. When the instrumentation is tracked using conventional tracking techniques, such as EM tracking, the location of the instrumentation in space is known. The imaging system described herein provides the location of the patient's imaged anatomy in space, so the present system knows the relative location of the instrument to that anatomy. However, it is known that distortion of EM signals occurs in a surgical and C-arm environment and that this distortion can distort the location of the instrument in the image. When the position of the instrument in space is known, by way of the tracking data, and the 2D plane of the x-ray image is known, as obtained by the present system, then the projection of the instrument onto that 2D plane can be readily determined. The imaged location of the instrument can then be corrected in the final image to eliminate the effects of distortion. In other words, if the location and position of the instrument is known from the tracking data and 3D model, then the location and position of the instrument on the 2D image can be corrected. One approach to correcting for distortion is described in the Appendix, the entire disclosure of which is incorporated herein by reference.

In certain procedures it is possible to fix the position of the vascular anatomy to larger features, such as nearby bones. This can be accomplished using DRRs from prior CT angiograms (CTA) or from actual angiograms taken in the course of the procedure. Either, approach may be used as a means to link angiograms back to bony anatomy and vice versa. To describe in greater detail, the same CTA may be used to produce different DRRs, such as DRRs highlighting just the bony anatomy and another in a matched set that includes the vascular anatomy along with the bones. A baseline fluoro image taken of the patient's bony anatomy can then be compared with the bone DRRs to determine the best match. Instead of displaying the result using bone only DRR, the matched DRR that includes the vascular anatomy can be used to merge with the new image. In this approach, the bones help to place the radiographic position of the catheter to its location within the vascular anatomy. Since it is not necessary to continually image the vessel itself, as the picture of this structure can be overlaid onto the bone only image obtained, the use of contrast dye can be limited versus prior procedures in which the contrast dye is necessary to constantly see the vessels.

Details of one approach to tracking the C-arm and instrumentation for use in the imaging and tracking functions of the present system are described in the Appendix, the entire description of which is incorporated herein by reference.

Following are examples of specific procedures utilizing the features of the image processing device discussed above. These are just a few examples as to how the software can be manipulated using different combinations of baseline image types, display options, and radiation dosing and not meant to be an exhaustive list.

Pulsed New Image/Alternated with/Baseline of FD Fluoro or Preoperative X-ray

A pulsed image is taken and compared with a previously obtained baseline image set containing higher resolution non-pulsed image(s) taken prior to the surgical procedure. Registration between the current image and one of the baseline solution set provides a baseline image reflecting the current position and view of the anatomy. The new image is alternately displayed or overlaid with the registered baseline image, showing the current information overlaid and alternating with the less obscured or clearer image.

Pulsed New Image/Alternated with/Baseline Derived from DRR

A pulsed image is taken and compared with a previously obtained solution set of baseline images, containing higher resolution DRR obtained from a CT scan. The DRR image can be limited to just show the bony anatomy, as opposed to the other obscuring information that frequently "cloud" a film taken in the OR (e.g.—bovie cords, EKG leads, etc.) as well as objects that obscure bony clarity (e.g.—bowel gas, organs, etc.). As with the above example, the new image that is registered with one of the prior DRR images, and these images are alternated or overlaid on the display 123, 124.

Pulsed New Image/Merged Instead of Alternated

All of the techniques described above can be applied and instead of alternating the new and registered baseline images, the prior and current image are merged. By performing a weighted average or similar merging technique, a single image can be obtained which shows both the current information (e.g.—placement of instruments, implants, catheters, etc.) in reference to the anatomy, merged with a higher resolution picture of the anatomy. In one example, multiple views of the merger of the two images can be provided, ranging from 100% pulsed image to 100% DRR image. A slide button on the user interface 125 allows the surgeon to adjust this merger range as desired.

New Image is a Small Segment of a Larger Baseline Image Set

The imaging taken at any given time contains limited information, a part of the whole body part. Collimation, for example, lowers the overall tissue radiation exposure and lowers the radiation scatter towards physicians but at the cost of limiting the field of view of the image obtained. Showing the actual last projected image within the context of a larger image (e.g.—obtained prior, preoperatively or intraoperatively, or derived from CTs)—merged or alternated in the correction location—can supplement the information about the smaller image area to allow for incorporation into reference to the larger body structure(s). The same image registration techniques are applied as described above, except that the registration is applied to a smaller field within the baseline images (stitched or not) corresponding to the area of view in the new image.

Same as Above, Located at Junctional or Blocked Areas

Not infrequently, especially in areas that have different overall densities (e.g.—chest vs. adjacent abdomen, head/neck/cervical spine vs. upper thorax), the area of an x-ray that can be clearly visualized is only part of the actual image obtained. This can be frustrating to the physician when it limits the ability to place the narrow view into the larger context of the body or when the area that needs to be evaluated is in the obscured part of the image. By stitching together multiple images, each taken in a localized ideal environment, a larger image can be obtained. Further, the current image can be added into the larger context (as described above) to fill in the part of the image clouded by its relative location.

Unblocking the Hidden Anatomy or Mitigating its Local Effects

As described above, the image processing device performs the image registration steps between the current new image and a baseline image set that, in effect, limits the misinformation imparted by noise, be it in the form of x-ray scatter or small blocking objects (e.g.—cords, etc.) or even larger objects (e.g.—tools, instrumentation, etc.). In many cases, it is that part of the anatomic image that is being blocked by a tool or instrument that is of upmost importance to the surgery being performed. By eliminating the blocking objects from the image the surgery becomes safer and more efficacious and the physician becomes empowered to continue with improved knowledge. Using an image that is taken prior to the noise being added (e.g.—old films, baseline single FD images, stitched together fluoro shots taken prior to surgery, etc.) or idealized (e.g. DRRs generated from CT data), displaying that prior "clean" image, either merged or alternated with the current image, will make those objects disappear from the image or become shadows rather than dense objects. If these are tracked objects, then the blocked area can be further deemphasized or the information from it can be eliminated as the mathematical comparison is being performed, further improving the speed and accuracy of the comparison.

The image processing device configured as described herein provides three general features that (1) reduce the amount of radiation exposure required for acceptable live images, (2) provide images to the surgeon that can facilitate the surgical procedure, and (3) improve the communication between the radiology technician and the surgeon. With respect to the aspect of reducing the radiation exposure, the present invention permits low dose images to be taken throughout the surgical procedure and fills in the gaps created by “noise” in the current image to produce a composite or merged image of the current field of view with the detail of a full dose image. In practice this allows for highly usable, high quality images of the patient’s anatomy generated with an order of magnitude reduction in radiation exposure than standard FD imaging using unmodified features present on all common, commercially available C-arms. The techniques for image registration described herein can be implemented in a graphic processing unit and can occur in a second or so to be truly interactive; when required such as in CINE mode, image registration can occur multiple times per second. A user interface allows the surgeon to determine the level of confidence required for acquiring registered image and gives the surgeon options on the nature of the display, ranging from side-by-side views to fade in/out merged views.

With respect to the feature of providing images to the surgeon that facilitate the surgical procedure, several digital imaging techniques can be used to improve the user’s experience. One example is an image tracking feature that can be used to maintain the image displayed to the surgeon in an essentially a “stationary” position regardless of any position changes that may occur between image captures. In accordance with this feature, the baseline image can be fixed in space and new images adjust to it rather than the converse. When successive images are taken during a step in a procedure each new image can be stabilized relative to the prior images so that the particular object of interest (e.g.—anatomy or instrument) is kept stationary in successive views. For example, as sequential images are taken as a bone screw is introduced into a body part, the body part remains stationary on the display screen so that the actual progress of the screw can be directly observed.

In another aspect of this feature, the current image including blocking objects can be compared to earlier images without any blocking objects. In the registration process, the image processing device can generate a merged image between new image and baseline image that deemphasizes the blocking nature of the object from the displayed image. The user interface also provides the physician with the capability to fade the blocking object in and out of the displayed view.

In other embodiments in which the object itself is being tracked, a virtual version of the blocking object can be added back to the displayed image. The image processing device can obtain position data from a tracking device following the position of the blocking object and use that position data to determine the proper location and orientation of the virtual object in the displayed image. The virtual object may be applied to a baseline image to be compared with a new current image to serve as a check step—if the new image matches the generated image (both tool and anatomy) within a given tolerance then the surgery can proceed. If the match is poor, the surgery can be stopped (in the case of automated surgery) and/or recalibration can take place. This allows for a closed-loop feedback feature to facilitate the safety of automation of medical intervention.

For certain procedures, such as a pseudo-angio procedure, projecting the vessels from a baseline image onto current image can allow a physician to watch a tool (e.g.—micro-catheter, stent, etc.) as it travels through the vasculature while using much less contrast medium load. The adjacent bony anatomy serves as the “anchor” for the vessels—the bone is essentially tracked, through the image registration process, and the vessel is assumed to stay adjacent to this structure. In other words, when the anatomy moves between successive images, the new image is registered to a different one of the baseline image set that corresponds to the new position of the “background” anatomy. The vessels from a different but already linked baseline image containing the vascular structures can then be overlaid or merged with the displayed image which lacks contrast. If necessary or desired, intermittent angios can be taken to confirm. When combined with a tracked catheter, a working knowledge of the location of the instrument can be included into the images. A cine (continuous movie loop of fluoro shots commonly used when an angiogram is obtained) can be created in which generated images are interspliced into the cine images, allowing for many fewer x-rays to be obtained while an angiogram is being performed or a catheter is being placed. Ultimately, once images have been linked to the original baseline image, any of these may be used to merge into a current image, producing a means to monitor movement of implants, the formation of constructs, the placement of stents, etc.

In the third feature—improving communication—the image processing device described herein allows the surgeon to annotate an image in a manner that can help guide the technician in the positioning of the C-arm as to how and where to take a new picture. Thus, the user interface 125 of the image processing device 122 provides a vehicle for the surgeon to add a grid to the displayed image, label anatomic structures and/or identify trajectories for alignment of the imaging device. As the technician moves the imaging device or C-arm, the displayed image is moved. This feature allows the radiology tech to center the anatomy that is desired to be imaged in the center of the screen, at the desired orientation, without taking multiple images each time the C-arm is brought back in the field to obtain this. This feature provides a view finder for the C-arm, a feature lacking currently. The technician can activate the C-arm to take a new image with a view tailored to meet the surgeon’s expressed need.

In addition, linking the movements of the C-arm to the images taken using DICOM data or a surgical navigation backbone, for example, helps to move the displayed image as the C-arm is moved in preparation for a subsequent image acquisition. “In bound” and “out of bounds” indicators can provide an immediate indication to the technician whether a current movement of the C-arm would result in an image that cannot be correlated or registered with any baseline image, or that cannot be stitched together with other images to form a composite field of view. The image processing device thus provides image displays that allow the surgeon and technician to visualize the effect of a proposed change in location and trajectory of the c-arm. Moreover, the image processing device may help the physician, for instance, alter the position of the table or the angle of the C-arm so that the anatomy is aligned properly (such as parallel or perpendicular to the surgical table). The image processing device can also determine the center of mass (COM) of the exact center of an x-rayed object using two or more x-ray shots from two or more different gantry angles/positions, and then use this COM information to improve the linking of the physical space (in millimeters) to the displayed imaging space (in pixels).

The image recognition component disclosed herein can overcome the lack of knowledge of the location of the next image to be taken, which provides a number of benefits. Knowing roughly where the new image is centered relative to the baseline can limit the need to scan a larger area of the imaging space and, therefore, significantly increase the speed of image recognition software. Greater amounts of radiation reduction (and therefore noise) can be tolerated, as there exists an internal check on the image recognition. Multiple features that are manual in the system designed without surgical navigation, such as baseline image creation, switching between multiple baseline image sets, and stitching, can be automated. These features are equally useful in an image tracking context.

As described above, the systems and methods correlate or synchronize the previously obtained images with the live images to ensure that an accurate view of the surgical site, anatomy and hardware, is presented to the surgeon. In an optimum case, the previously obtained images are from the particular patient and are obtained near in time to the surgical procedure. However, in some cases no such prior image is available. In such cases, the "previously obtained image" can be extracted from a database of CT and DRR images. The anatomy of most patients is relatively uniform depending on the height and stature of the patient. From a large database of images there is a high likelihood that a prior image or images of a patient having substantially similar anatomy can be obtained. The image or images can be correlated to the current imaging device location and view, via software implemented by the image processing device 122, to determine if the prior image is sufficiently close to the anatomy of the present patient to reliably serve as the "previously obtained image" to be interspliced with the live images.

The display in FIG. 10 is indicative of the type of display and user interface that may be incorporated into the image processing device 122, user interface 125 and display device 126. For instance, the display device may include the two displays 122, 123 with "radio" buttons or icons around the perimeter of the display. The icons may be touch screen buttons to activate the particular feature, such as the "label", "grid" and "trajectory" features shown in the display. Activating a touch screen or radio button can access a different screen or pull down menu that can be used by the surgeon to conduct the particular activity. For instance, activating the "label" button may access a pull down menu with the labels "L1", "L2", etc., and a drag and drop feature that allows the surgeon to place the labels at a desire location on the image. The same process may be used for placing the grid and trajectory arrows shown in FIG. 10.

Figures 12A, 12B:
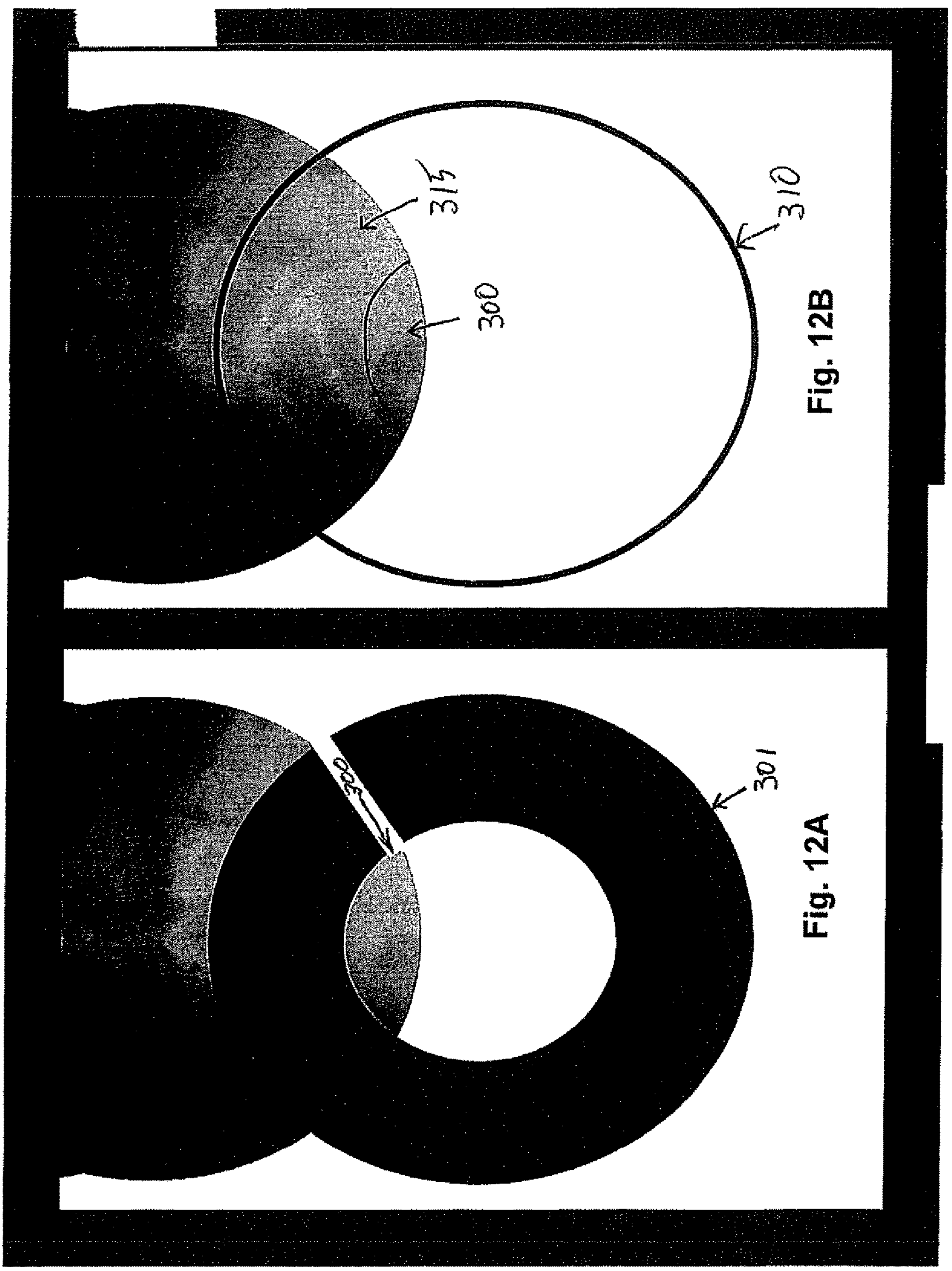
FIG. 12A is an image of a surgical field obtained through a collimator.
FIG. 12B is an image of the surgical field shown in FIG. 12A as enhanced by the systems and methods disclosed herein.
Figures 13A, 13B:
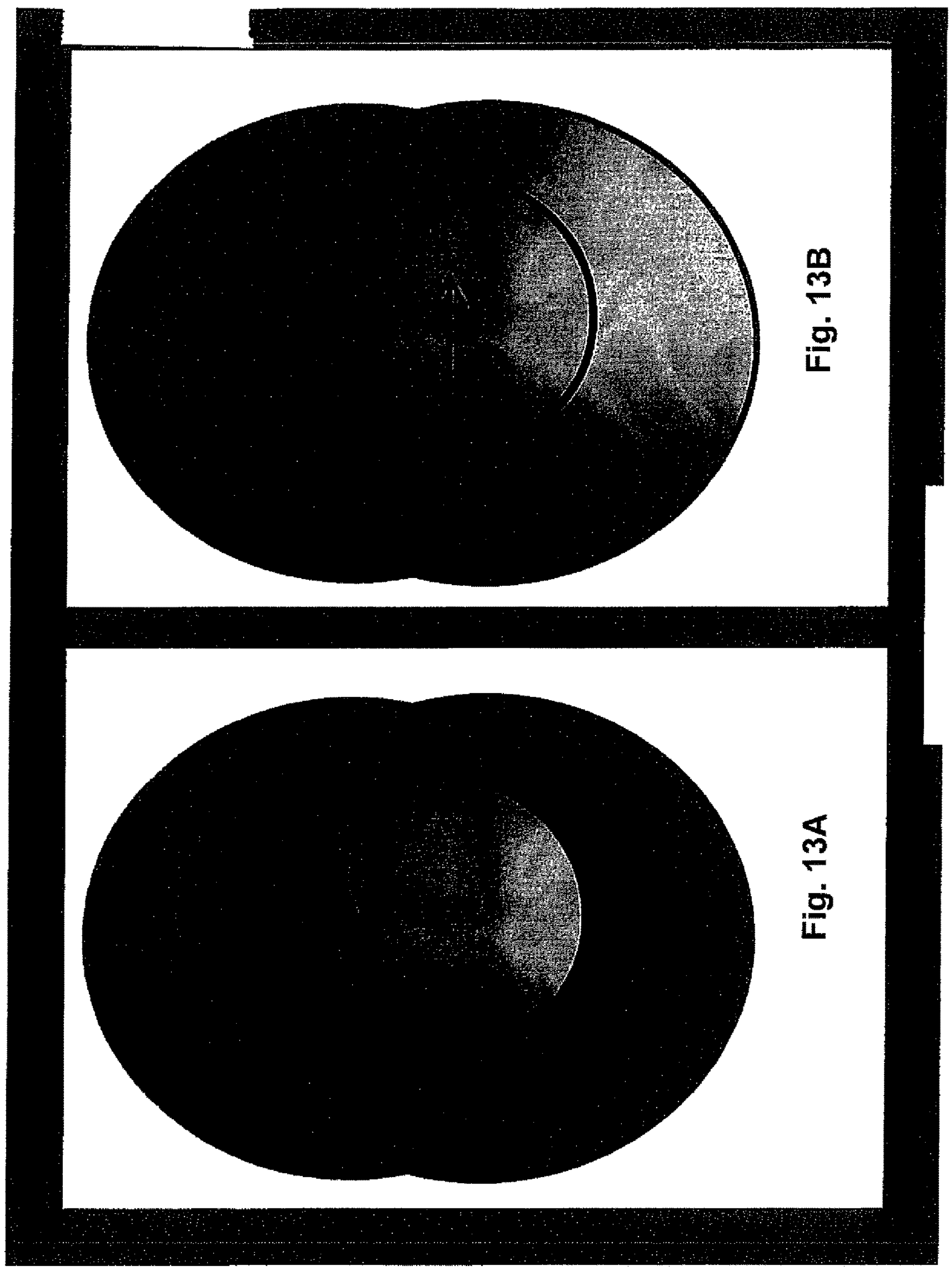
FIG. 13A, FIG. 13B, FIG. 14A, FIG. 14B, FIG. 15A, FIG. 15B, FIG. 16A and FIG. 16B are images showing a surgical field obtained through a collimator in which the collimator is moved
Figures 14A, 14B:
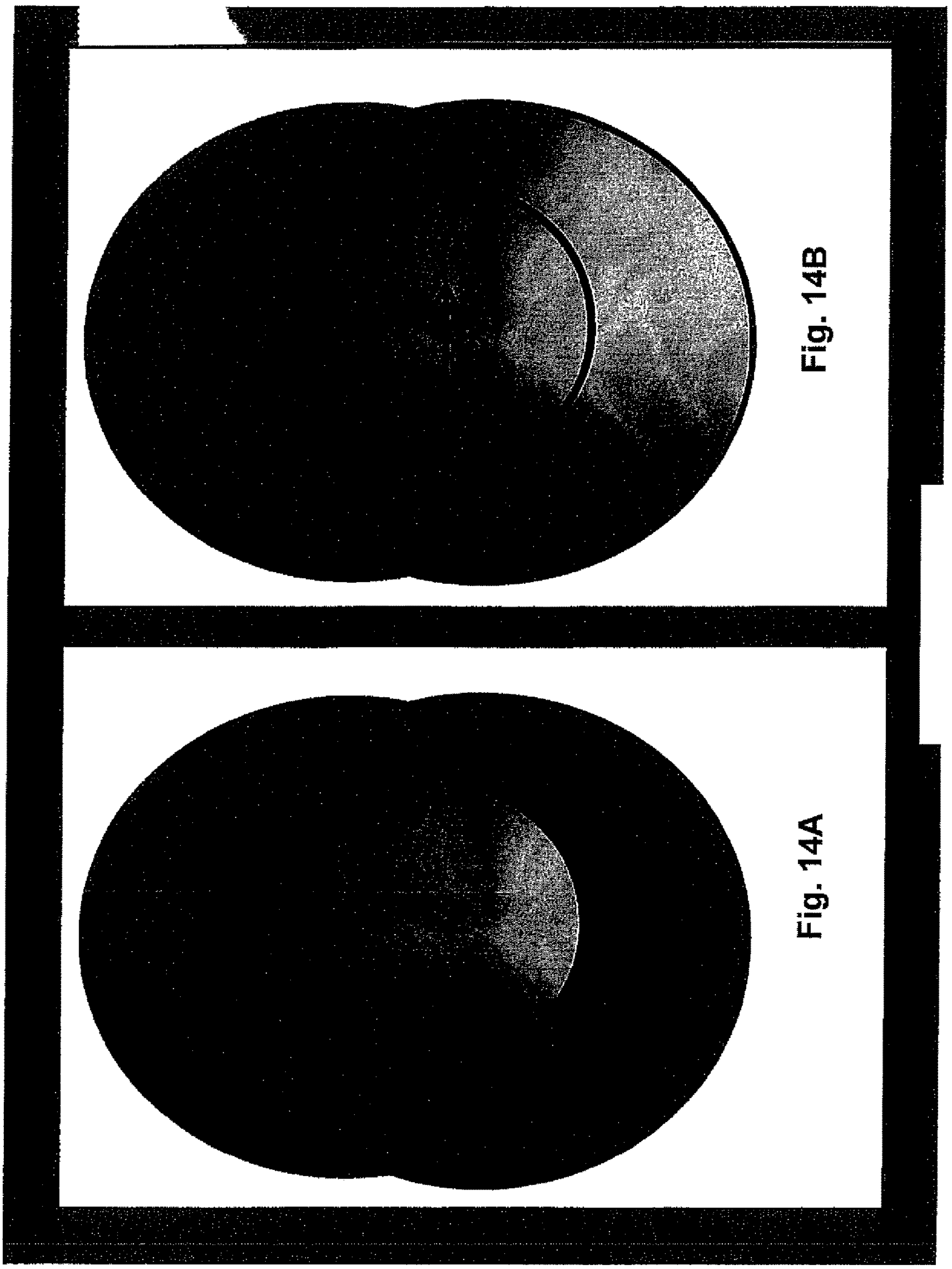
Figures 15A, 15B:
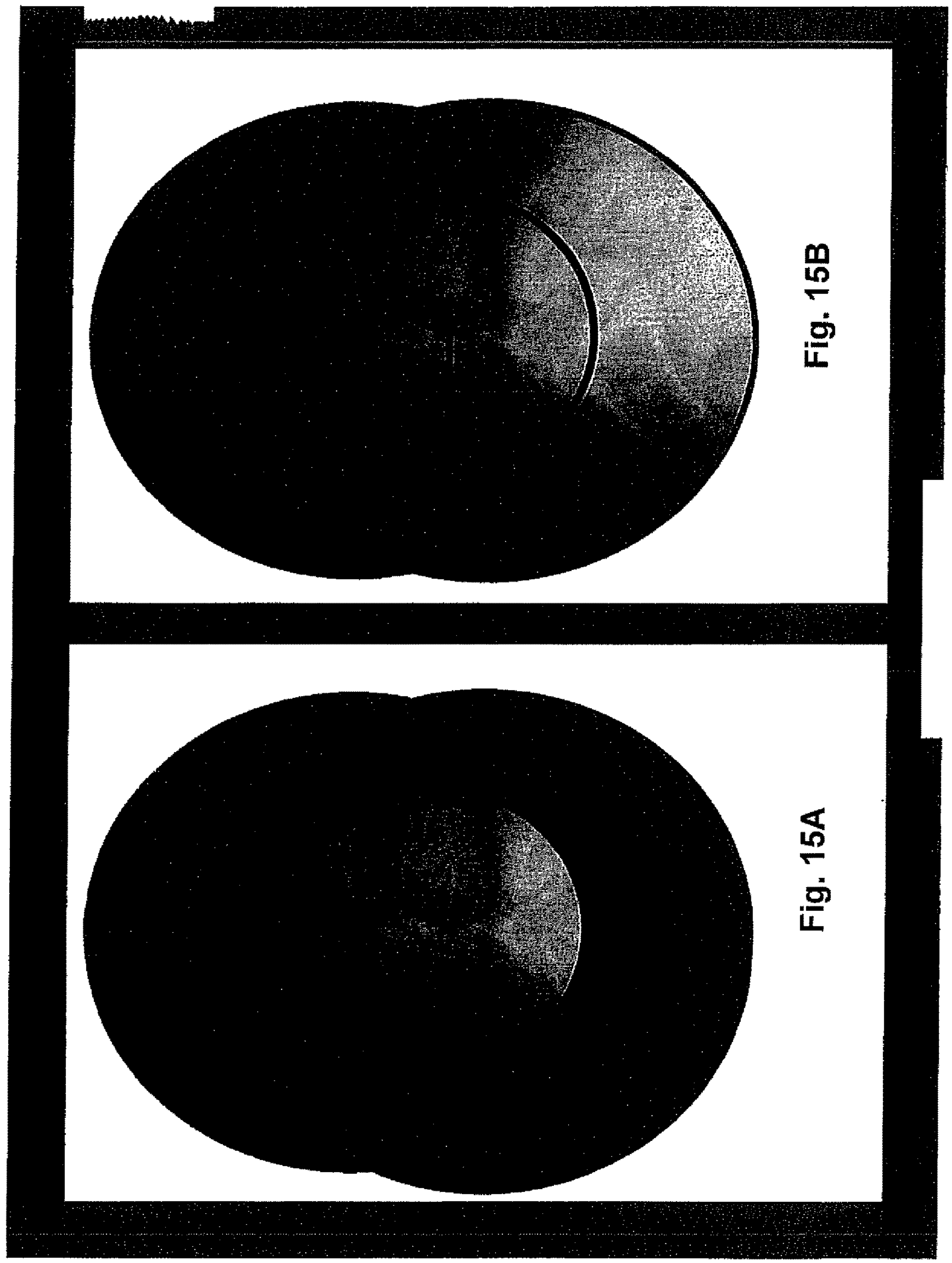
Figures 16A, 16B:
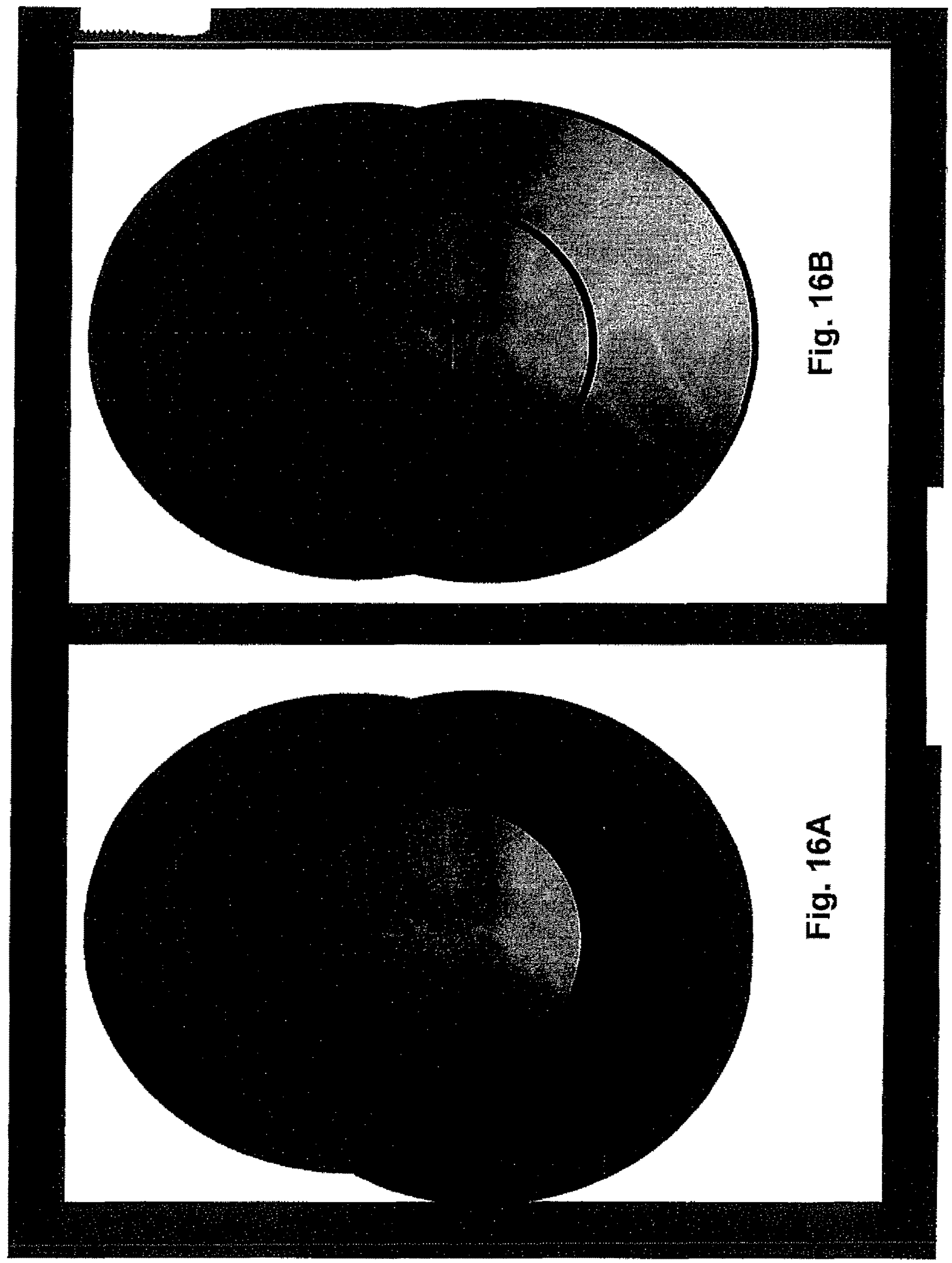

The same system and techniques described above may be implemented where a collimator is used to reduce the field of exposure of the patient. For instance, as shown in FIG. 12A, a collimator may be used to limit the field of exposure to the area 300 which presumably contains the critical anatomy to be visualized by the surgeon or medical personnel. As is apparent from FIG. 12A the collimator prevents viewing the region 301 that is covered by the plates of the collimator. Using the system and methods described above, prior images of the area 315 outside the collimated area 300 are not visible to the surgeon in the expanded field of view 310 provided by the present system.

The same principles may be applied for images obtained using a moving collimator. As depicted in the sequence of FIGS. 13A, 14A, 15A and 16A the visible field is gradually shifted to the left in the figures as the medical personnel zeroes in on a particular part of the anatomy. Using the system and methods described herein, the image available to the medial personnel is shown in FIGS. 13B, 14B, 15B and 16B in which the entire local anatomy is visible. It should be understood that only the collimated region (i.e. region 300 in FIG. 12A) is a real-time image. The image outside the collimated region is obtained from previous images as described above. Thus, the patient is still subject to a reduced dosage of radiation while the medical personnel is provided with a complete view of the relevant anatomy. As described above, the current image can be merged with the baseline or prior image, can be alternated or even displayed un-enhanced by imaging techniques described herein.

The present disclosure contemplates a system and method in which information that would otherwise be lost because it is blocked by a collimator, is made available to the surgeon or medical personnel interactively during the procedure. Moreover, the systems and methods described herein can be used to limit the radiation applied in the non-collimated region. These techniques can be applied whether the imaging system or collimator are held stationary or are moving.

In a further aspect, the systems and methods described herein may be incorporated into an image-based approach for controlling the state of a collimator in order to reduce patient exposure to X-rays during surgical procedures that require multiple X-ray images of the same anatomical region. In particular, the boundaries of the aperture of the collimator are determined by the location of the anatomical features of interest in previously acquired images. Those parts of the image that are not important to the surgical procedure can be blocked by the collimator, but then filled in with the corresponding information from the previously acquired images, using the systems and methods described above and in published application US-2012-0087562-A1. The collimated image and the previous images can be displayed on the screen in a single merged view, they can be alternated, or the collimated image can be overlaid on the previous image. To properly align the collimated image with the previous image, image-based registration similar to that described in published application US-2012-0087562-A1 can be employed.

In one approach, the anatomical features of interest can be determined manually by the user drawing a region of interest on a baseline or previously obtained image. In another approach, an object of interest in the image is identified, and the collimation follows the object as it moves through the image. When the geometric state of the X-ray system is known, the movement of the features of interest in the detector field of view can be tracked while the system moves with respect to the patient, and the collimator aperture can be adjusted accordingly, as illustrated in FIGS. 13A, 13B, 14A, 14B, 15A, 15B, 16A, 16B. The geometric state of the system can be determined with a variety of methods, including optical tracking, electromagnetic tracking, and accelerometers.

In another aspect of the present disclosure, the systems and methods described herein and in published application US-2012-0087562-A1 can be employed to control radiation dosage. An X-ray tube consists of a vacuum tube with a cathode and an anode at opposite ends. When an electric current is supplied to the cathode, and a voltage is applied across the tube, a beam of electrons travels from the cathode to the anode and strikes a metal target. The collisions of the electrons with the metal atoms in the target produce X-rays, which are emitted from the tube and used for imaging. The strength of the emitted radiation is determined by the current, voltage, and duration of the pulses of the beam of electrons. In most medical imaging systems, such as C-arms, these parameters are controlled by an automatic exposure control (AEC) system. This system uses a brief initial pulse in order to generate a test image, which can be used to subsequently optimize the parameters for maximizing image clarity while minimizing radiation dosage.

One problem with existing AEC systems is that they do not account for the ability of image processing software to exploit the persistence of anatomical features in medical images in order to achieve further improvements in image clarity and reductions in radiation dosage. This techniques described herein utilize software and hardware elements to continuously receive the images produced by the imaging system and refine these images by combining them with images acquired at previous times. The software elements also compute an image quality metric and estimates how much the radiation exposure can be increased or decreased for the metric to achieve a certain ideal value. This value is determined by studies of physician evaluations of libraries of medical images acquired at various exposure settings, and may be provided in a table look-up stored in a system memory accessible by the software elements, for example. The software converts the estimated changes to the amounts of emitted radiation into exact values for the voltage and current to be applied to the X-ray tube. The hardware element consists of an interface from the computer running the image processing software to the controls of the X-ray tube that bypasses the AEC and sets the voltage and current.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method for generating a display of an image of a patient's internal anatomy in a surgical field during a medical procedure, comprising:

acquiring a high resolution baseline image of a surgical field including the patient's internal anatomy in a baseline orientation;

acquiring a first low resolution baseline image of the surgical field and a first surgical instrument;

acquiring a second low resolution baseline image of the surgical field, the first surgical instrument, and a second surgical instrument;

determining a representation of the second surgical instrument based on an analysis of the first low resolution baseline image and the second low resolution baseline image;

determining a virtual outline of the second surgical instrument based on information indicative of a digital model of the second surgical instrument;

matching at least a portion of the virtual outline of the second surgical instrument to an outline of the representation of the second surgical instrument;

overlaying the representation of the second surgical instrument onto the high resolution baseline image; and displaying the overlaid representation of the second surgical instrument onto the high resolution baseline image.

2. The method of claim 1, wherein determining the representation of the second surgical instrument further comprises:

determining a first outline of the first surgical instrument according to the first low resolution baseline image;

determining a second outline of (i) the first surgical instrument and (ii) the second surgical instrument according to the second low resolution baseline image; and determining a third outline of the second surgical instrument based on a comparison of the first outline and the second outline.

3. The method of claim 1, wherein determining the third outline further comprises subtracting the first outline from the second outline.

4. The method of claim 1, wherein the high resolution baseline image, the first low resolution baseline image, and the second low resolution baseline image are computerized tomography scans.

5. The method of claim 1, wherein overlaying the representation of the second surgical instrument further comprises overlaying the virtual outline of the second surgical instrument onto the high resolution baseline image.

6. The method of claim 1, wherein the high resolution baseline image is captured at a first radiation exposure, the first low resolution baseline image is captured at a second radiation exposure, and the second low resolution baseline image is captured at the second radiation exposure, wherein the second radiation exposure is less than the first radiation exposure.

7. A method for generating a display of an image of a patient's internal anatomy in a surgical field during a medical procedure, comprising:

acquiring a first high resolution baseline image of a surgical field with an x-ray imaging device, wherein the first high resolution baseline image includes the patient's internal anatomy in a baseline orientation;

acquiring a second high resolution baseline image of (i) the surgical field and (ii) a first surgical instrument with the x-ray imaging device;

determining a two-dimensional representation of the first surgical instrument based on an analysis of the first high resolution baseline image and the second resolution baseline image;

acquiring a low resolution baseline image of (i) the surgical field, (ii) the first surgical instrument, and (iii) a second surgical instrument with the x-ray imaging device;

determining a two-dimensional representation of the second surgical instrument based on an analysis of the second high resolution baseline image and the low resolution baseline image;

determining a virtual outline of the second surgical instrument based on information indicative of a digital model of the second surgical instrument;

matching at least a portion of the virtual outline of the second surgical instrument to an outline of the two-dimensional representation of the second surgical instrument;

overlaying the two-dimensional representation of first surgical instrument and the two-dimensional representation of the second surgical instrument onto the high resolution baseline image; and displaying the representation of the first surgical instrument at a first opacity and the representation of the second surgical instrument at a second opacity onto the high resolution baseline image.

8. The method of claim 7, wherein determining the representation of the second surgical instrument further comprises:

determining a first outline of the first surgical instrument according to the second high resolution baseline image;

determining a second outline of (i) the first surgical instrument and (ii) the second surgical instrument according to the low resolution baseline image; and determining a third outline of the second surgical instrument based on a comparison of the first outline and the second outline.

9. The method of claim 8, wherein determining the third outline further comprises subtracting the first outline from the second outline.

10. The method of claim 7, wherein the first high resolution baseline image, the second high resolution baseline image, and the low resolution baseline image are computerized tomography scans.

11. The method of claim 7, wherein overlaying the representation of the second surgical instrument further comprises overlaying the virtual outline of the second surgical instrument onto the high resolution baseline image.

12. The method of claim 7, wherein the first high resolution baseline image and the second high resolution baseline image are captured at a first radiation exposure, wherein the low resolution baseline image is captured at a second radiation exposure, wherein the second radiation exposure is less than the first radiation exposure.

13. The method of claim 7, wherein the x-ray imaging device is a C-Arm.

14. An apparatus for generating a display of an image of a patient's internal anatomy in a surgical field during a medical procedure, wherein the apparatus is configured to:

acquire a high resolution baseline image of a surgical field including the patient's internal anatomy in a baseline orientation;

acquire a first low resolution baseline image of the surgical field and a first surgical instrument;

acquire a second low resolution baseline image of the surgical field, the first surgical instrument, and a second surgical instrument;

determine a representation of the second surgical instrument based on an analysis of the first low resolution baseline image and the second low resolution baseline image;

determine a virtual outline of the second surgical instrument based on information indicative of a digital model of the second surgical instrument;

match at least a portion of the virtual outline of the second surgical instrument to an outline of the representation of the second surgical instrument;

overlay the representation of the second surgical instrument onto the high resolution baseline image; and provide instructions to display the overlaid representation of the second surgical instrument onto the high resolution baseline image.

15. The apparatus of claim 14, wherein the apparatus is further configured to:

determine a first outline of the first surgical instrument according to the first low resolution baseline image;

determine a second outline of (i) the first surgical instrument and (ii) the second surgical instrument according to the second low resolution baseline image; and determine a third outline of the second surgical instrument based on a comparison of the first outline and the second outline.

16. The apparatus of claim 15, wherein the step to determine the third outline further comprises subtracting the first outline from the second outline.

17. The apparatus of claim 14, wherein the high resolution baseline image, the first low resolution baseline image, and the second low resolution baseline image are computerized tomography scans.

* * * * *